United States Patent [19]

Haber et al.

[11] Patent Number: 5,078,699
[45] Date of Patent: Jan. 7, 1992

[54] COMPACT, EASY TO ASSEMBLE, SAFETY IV SYSTEM

[75] Inventors: Terry M. Haber, El Toro; Clark B. Foster, Laguna Niguel; William H. Smedley, Lake Elsinore, all of Calif.

[73] Assignee: Habley Medical Technology Corporation, Laguna Hills, Calif.

[21] Appl. No.: 410,927

[22] Filed: Sep. 22, 1989

[51] Int. Cl.$^5$ .............................................. A61M 5/00
[52] U.S. Cl. ...................................... 604/250; 604/80; 604/82
[58] Field of Search ............... 604/250, 251, 253, 255, 604/256, 262, 408, 410, 80, 81, 82, 83

[56] References Cited

U.S. PATENT DOCUMENTS

| | | | |
|---|---|---|---|
| 4,403,992 | 9/1983 | Bertellini et al. | 604/410 |
| 4,410,026 | 10/1983 | Boggs et al. | 604/262 X |
| 4,869,457 | 9/1989 | Ewerlof | 604/250 |
| 4,869,721 | 9/1989 | Karpisek | 604/250 |
| 4,943,288 | 7/1990 | Kurtz et al. | 604/408 |
| 4,960,259 | 10/1990 | Sunnanvader et al. | 604/250 |

Primary Examiner—John D. Yasko
Attorney, Agent, or Firm—Hawes & Fischer

[57] ABSTRACT

An improved IV system comprising one or more medication bags in which fluid is packaged, a safety IV catheter assembly for delivering fluid from the medication bags to the patient, and a quick-disconnect fluid coupler by which fluid tubing from respective medication bags may be quickly and efficiently connected to fluid tubing associated with the catheter assembly. Each medication bag includes an integral flow control device and drip chamber by which to accurately and selectively regulate the rate at which fluid is supplied to the catheter assembly. The catheter assembly includes a detachable and disposable safety housing into which a solid core trocar can be withdrawn and shielded after making a veni puncture through the patient's tissue. The fluid coupler includes a pair of locking fingers that are rotated through respective locking perforations located adjacent the fluid tube to which the coupler is to be connected. A hollow fluid cannula extends from the coupler into the fluid tube so as to establish a flow path therebetween.

22 Claims, 13 Drawing Sheets

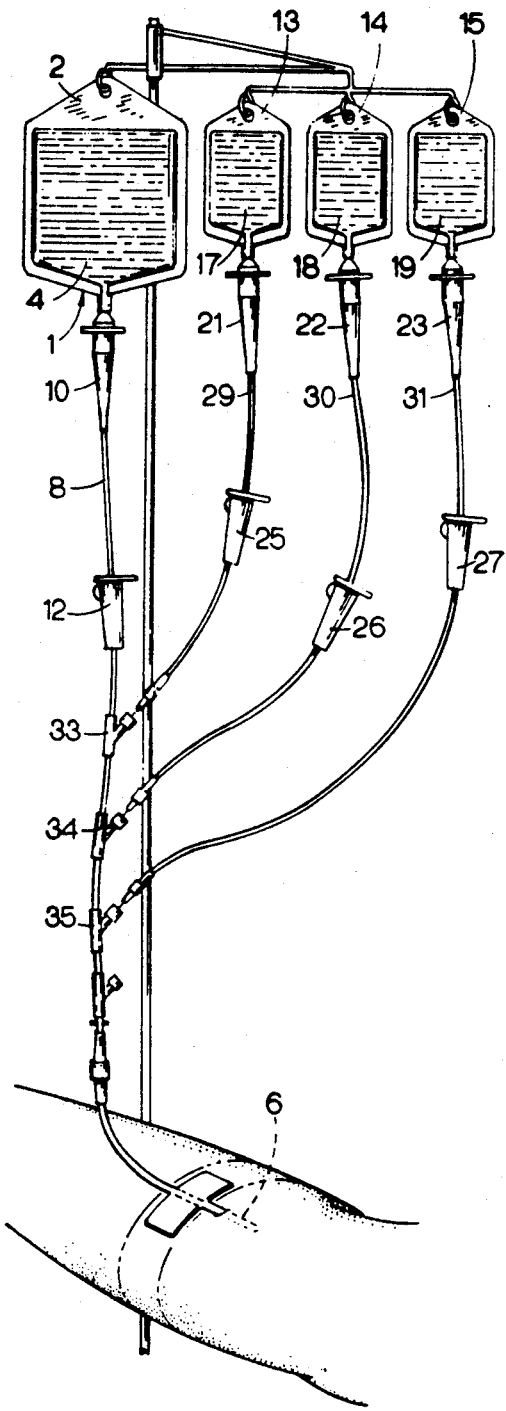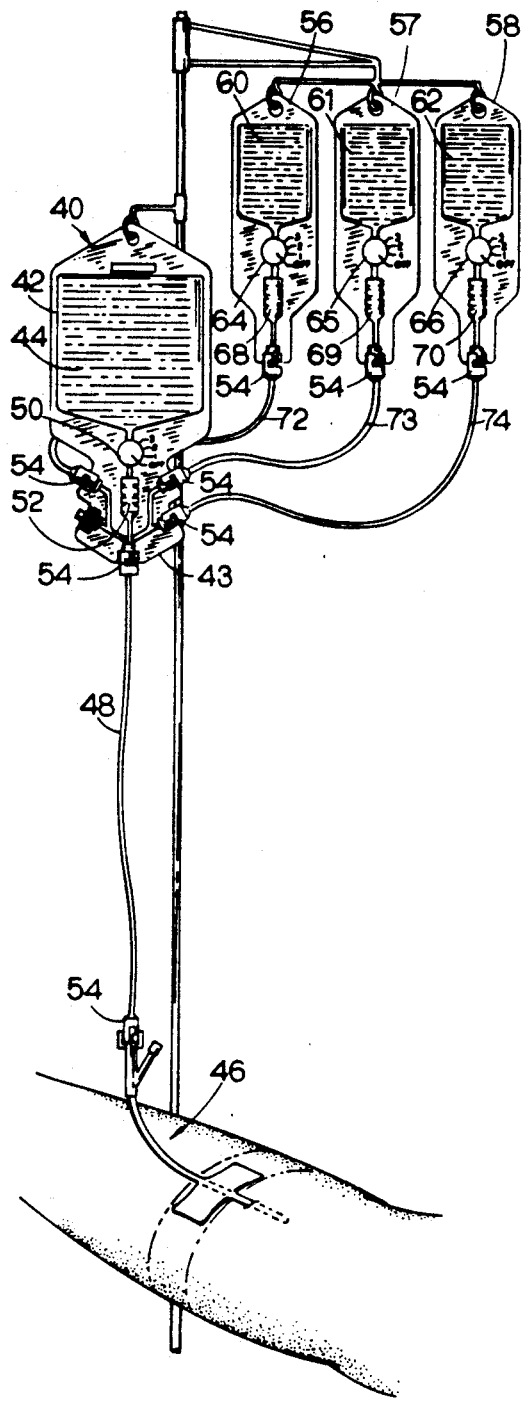
FIG. 1
FIG. 2

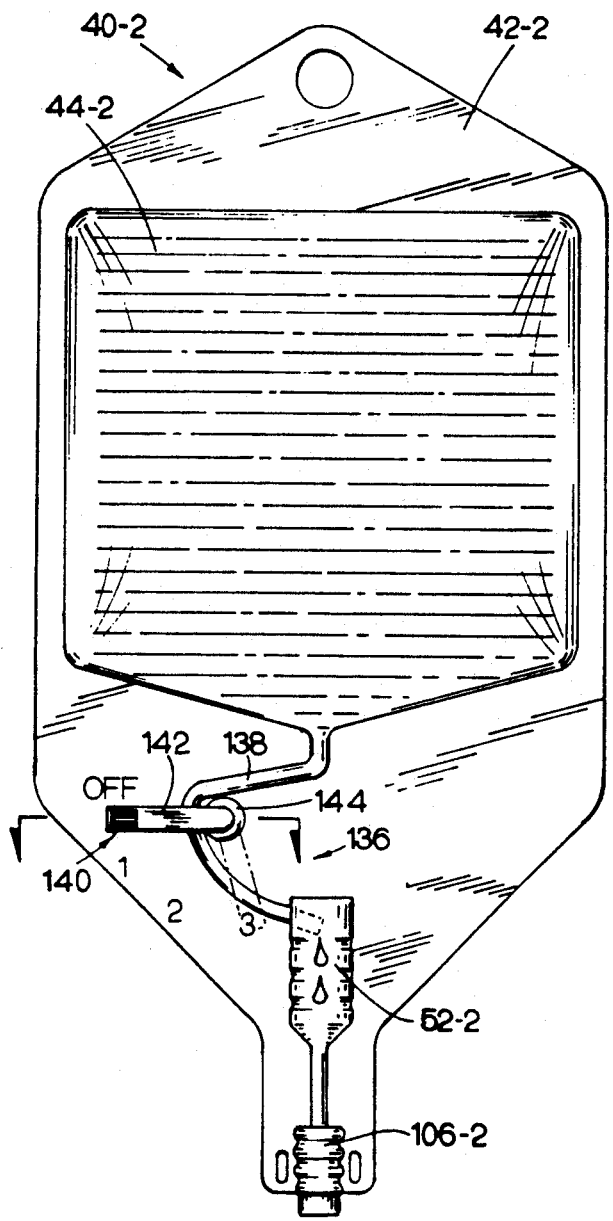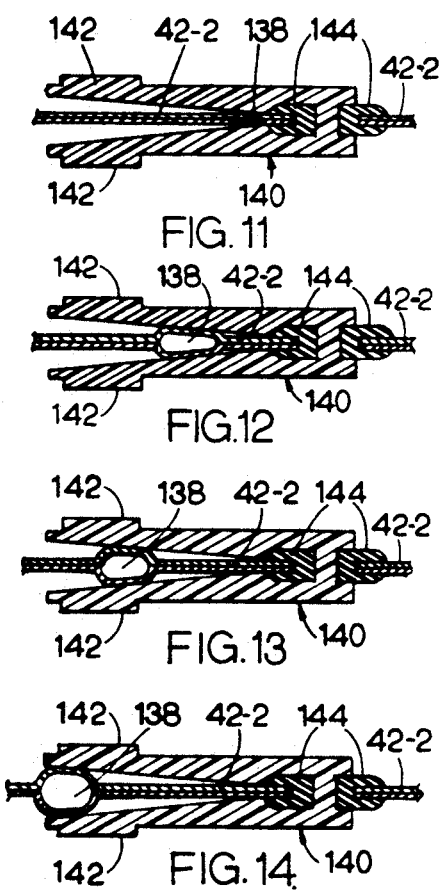
FIG. 10
FIG. 11
FIG. 12
FIG. 13
FIG. 14

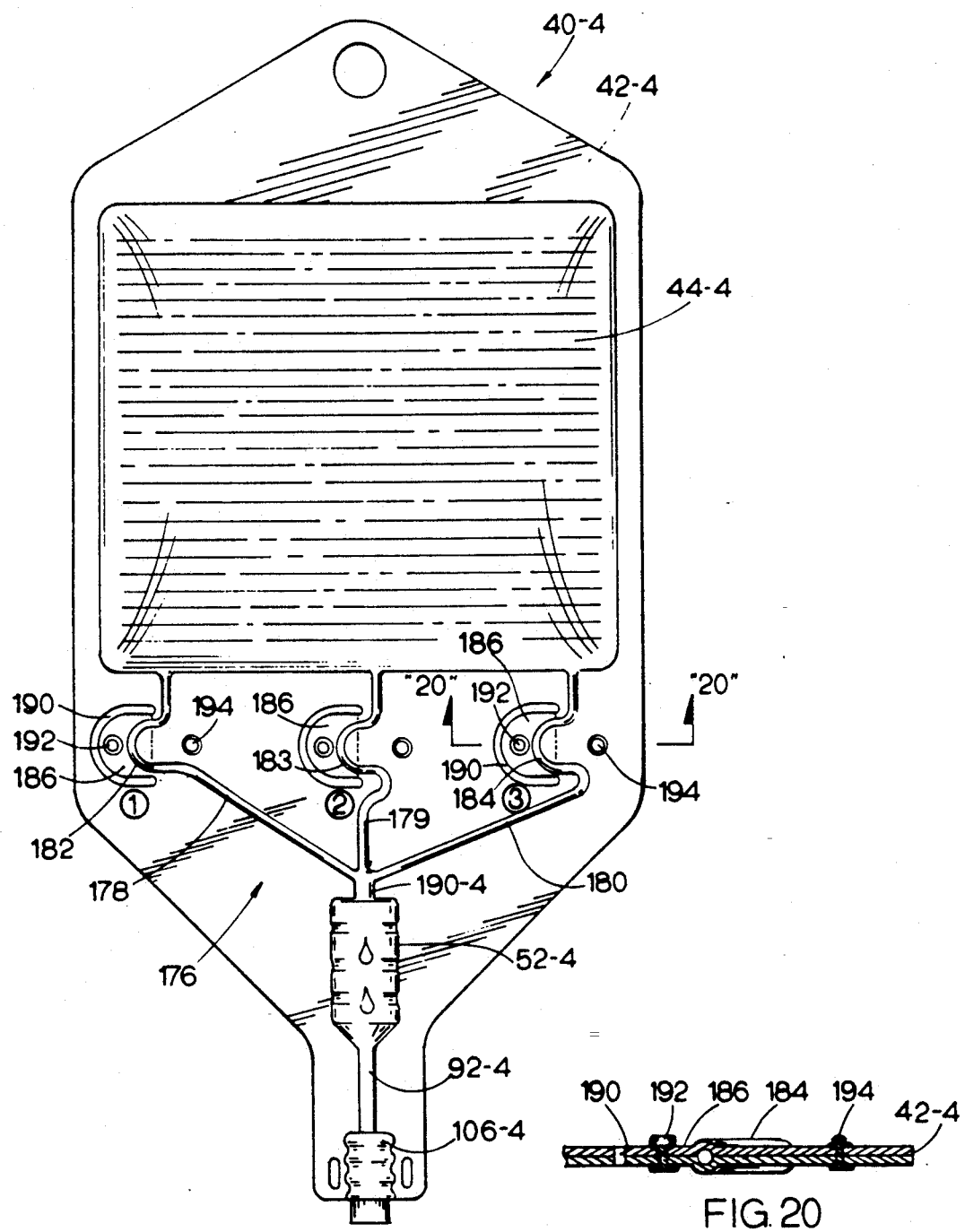
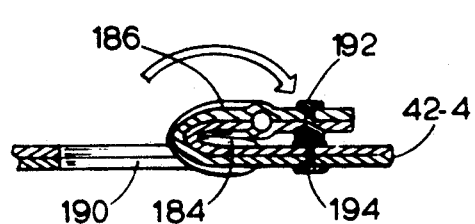
FIG. 19
FIG. 20
FIG. 21

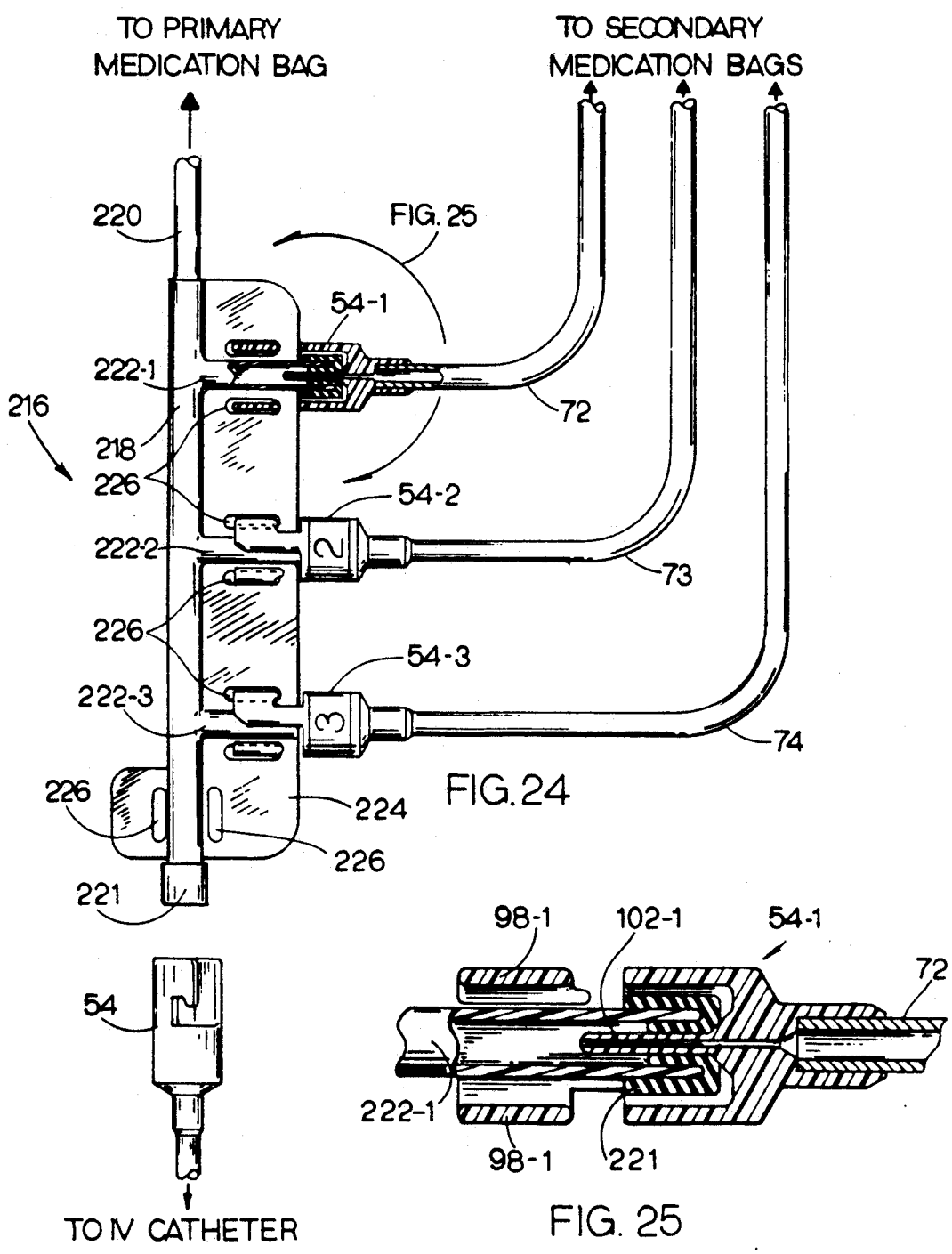

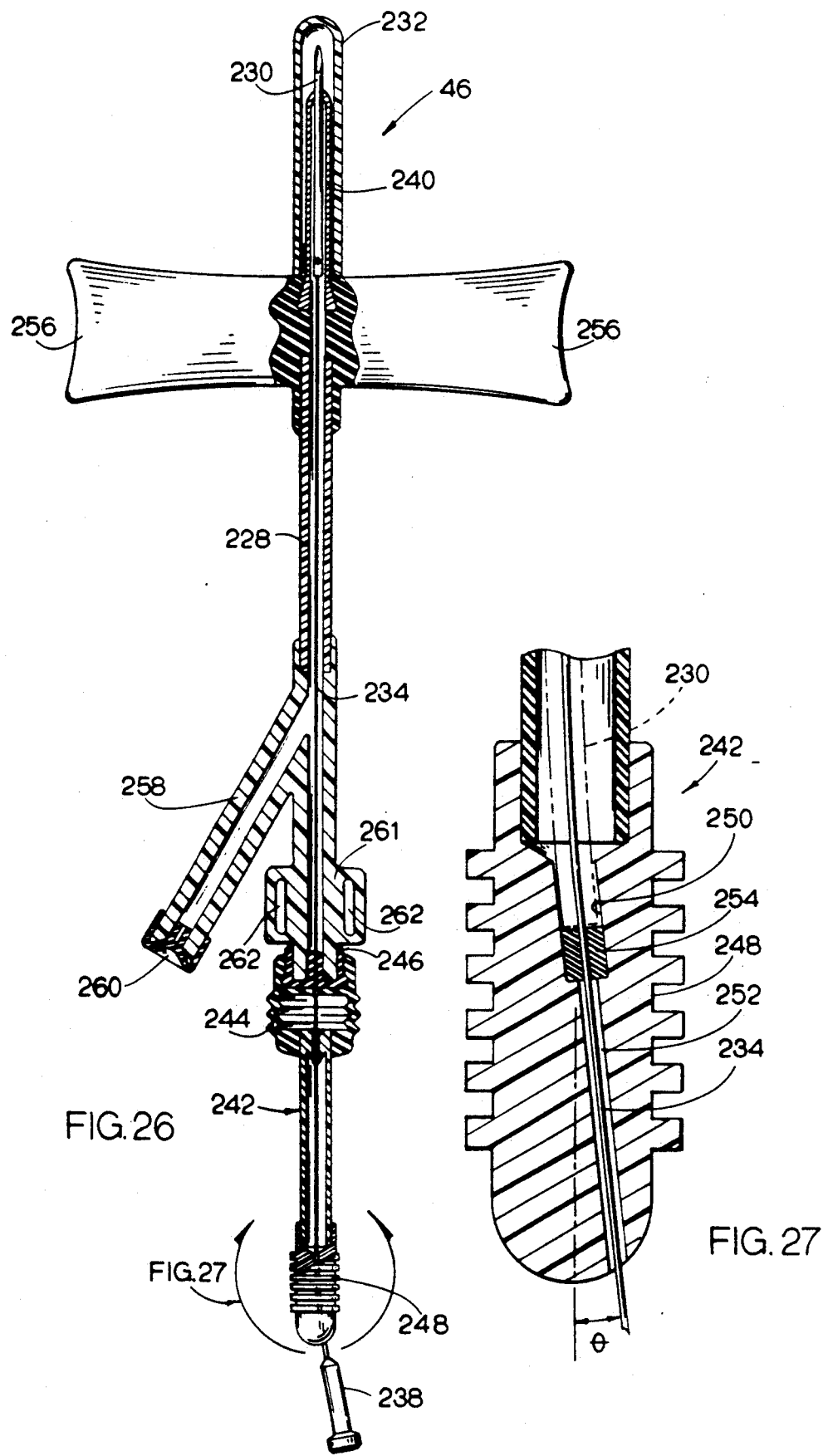

COMPACT, EASY TO ASSEMBLE, SAFETY IV SYSTEM

BACKGROUND OF THE INVENTION

1. Field of the Invention

This invention relates to an improved IV system that is characterized by a compact arrangement and reduced number of parts, improved efficiency and ease of assembly, and enhanced safety so as to avoid the spread of infection as a consequence of treating a patient having a communicable disease.

2. Background Art

IV systems are well known for use in hospitals and other medical facilities for delivering fluid from one or more medication bags to a patient by means of an IV catheter. However, conventional IV systems are characterized by several significant shortcomings. For example, conventional systems are typically formed from a large assortment of discrete parts and long fluid tubes which must be carefully assembled prior to use. A health care worker may encounter both difficulty and loss of time when completing the assembly, particularly when a number of medication bags and fluid tubes must be interconnected. Moreover, the use of many discrete parts increases the cost as well as the complexity of the system. In addition, there is no reliable way known by which to precisely regulate the rate at which fluid flows from a medication bag to an IV catheter. That is, the fluid flow rate from the medication bag may fluctuate due to design flaws in existing drip chambers, or the flow rate available with existing drip chamber configurations may be inadequate to meet certain needs of the patient.

Another significant problem inherent with conventional IV systems is accidental needle sticks and the possible spread of a contagious disease, such as AIDS, hepatitis and the like. More particularly, a sharp trocar is usually employed to make a veni puncture through the patient's tissue so that an IV catheter can be placed into the patient's vein. After making the veni puncture, it is common to remove the trocar for disposal in an unshielded condition. The careless handling and/or disposal of such trocar could subject the health care worker to an accidental needle stick and to possible infection.

What is more, when the trocar is removed, blood frequently rushes unchecked from the patient's vein through the catheter, before the catheter can be connected to an IV fluid line. This condition, sometimes known as blood backflash, can also expose the health care worker, as well as other patients, to infection as a consequence of treating a patient with a blood related disease.

SUMMARY OF THE INVENTION

In general terms, a compact, relatively easy to assemble, and enhanced safety IV system is disclosed by which fluid can be delivered from one or more fluid filled bags to a patient by way of a catheter assembly. At least one of the fluid bags includes an integral flow control device and drip chamber so that the rate at which fluid is delivered to the catheter assembly can be accurately and selectively regulated. A fluid tube extends between a fluid filled bladder of the medication bag and the integral drip chamber. In general terms, the flow control device includes means by which to apply a compressive force to said fluid tube to thereby vary the cross-sectional flow area thereof. That is, the rate at which fluid flows through the tube can be selectively adjusted from a maximum rate, at which the compressive force is removed so that the tube is completely open to fluid flow, to a minimum rate, at which the compressive force is maximized so that the tube is closed to fluid flow. More particularly, and by way of a preferred embodiment, the flow control device includes a rotatable pressure regulating knob having a pressure inducing stem projecting therefrom in spaced alignment with the fluid tube to be controlled. As the pressure regulating knob is rotated, the pressure inducing stem is moved axially towards and into contact with the fluid tube. The cross-sectional flow area of the fluid tube is adjusted by rotating the knob and thereby causing a corresponding movement of the stem relative to the tube.

The IV catheter assembly includes a disposable safety housing and a removable trocar which is to be relocated from an axially extended position, at which to make a veni puncture through the patient's tissue, to a retracted position within the safety housing, where said trocar is completely surrounded and safely shielded. The safety housing is detached from the catheter assembly and disposed with the trocar rendered inaccessible therein. Accordingly, handling of the trocar is eliminated, whereby an accidental needle stick and the spread of contagious disease, as a consequence thereof, can be advantageously avoided.

A unique fluid coupler is also disclosed by which the fluid tubing of the presently described IV system can be quickly and easily interconnected The coupler includes a pair of oppositely disposed locking fingers that are rotatable through respective locking perforations so that a hollow fluid cannula of the coupler will be received within a fluid tube with which a flow path is to be established. The locking perforations are located in a support platen in which the fluid tube is formed. The support platen may be an integral part of either a medication bag or a fluid manifold having a plurality of such fluid tubes.

BRIEF DESCRIPTION OF THE DRAWINGS

FIG. 1 shows a conventional IV system;

FIG. 2 shows the compact, easy to assemble and safety IV system of the present invention;

FIG. 10 shows a fluid medication bag having a fluid flow control device that is formed in accordance with another embodiment of the present invention;

FIGS. 11-14 illustrate the operation of the flow control device of FIG. 10 for regulating the rate at which fluid flows from the medication bag of FIG. 10 from a minimum to a maximum flow rate;

FIG. 19 shows a fluid medication bag having a fluid flow control device that is formed in accordance with still another embodiment of the present invention;

FIG. 20 is a cross-section taken along lines 20—20 of FIG. 19;

FIG. 21 illustrates the flow control device of FIG. 20 rotated to a locked position so as to control the rate at which fluid flows from the medication bag of FIG. 19;

FIG. 24 shows a fluid manifold by which a plurality of fluid tubes from the presently disclosed IV system may be easily and efficiently interconnected;

FIG. 25 shows an enlargement of a detail illustrated in FIG. 24;

FIG. 26 is a safety IV catheter assembly that is formed in accordance with a preferred embodiment of the present invention;

FIG. 27 shows an enlargement of a detail illustrated in FIG. 26;

DESCRIPTION OF THE PREFERRED EMBODIMENT

Figure 3:
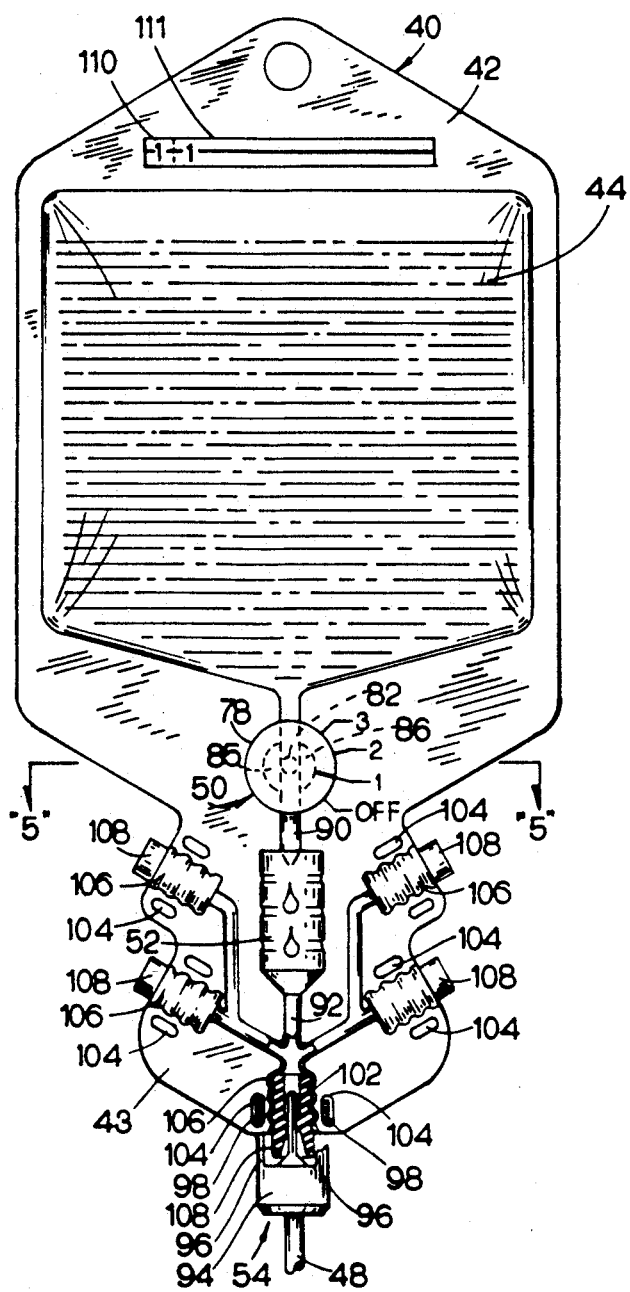
FIG. 3 shows a fluid medication bag from the Iv system of FIG. 2 having a flow control device that is formed in accordance with a preferred embodiment of the present invention.

FIG. 1 of the drawings shows a conventional IV system. Such a conventional system comprises a primary medication bag 1 including a typically soft, flexible platen 2 which surrounds and supports a fluid filled bladder 4. The bladder 4 communicates with and supplies fluid to a catheter 6 by way of a main IV fluid line 8. Connected into main fluid line 8 to control the volume and rate of fluid flow are a discrete drip chamber 10 and a discrete flow control device 12. For purposes of illustration, the IV system of FIG. 1 also includes a plurality of (e.g. three) secondary medication bags 13-15, each having a respective fluid filled bladder 17-19. Discrete drip chambers 21-23 and flow control devices 25-27 are located in respective secondary fluid lines 29-31. Each secondary fluid line 29-31 is fluidically coupled to the main fluid line 8 by way of conventional Y-connectors 33-35. As should be apparent, the conventional IV system of FIG. 1 consists of many discrete parts and long fluid lines which increase the cost and complexity of the system. Moreover, the conventional system of FIG. 1 may also prove to be relatively difficult and time consuming to assemble.

FIG. 2 of the drawings shows the safety IV system which forms a preferred embodiment of the present invention and which is characterized by a relatively few number of parts, a lower overall cost, improved safety, and simplicity of assembly, as compared to the conventional system of FIG. 1. The safety IV system of the present invention includes a primary medication bag 40 having a soft flexible platen 42 which surrounds and supports a fluid filled bladder 44. Coextensively formed within and projecting distally from platen 42 is a relatively narrow platen appendage 43. The bladder 44 communicates with a soon to be described anti-blood flashback catheter assembly 46 by way of a main IV fluid line 48. Unlike the medication bag of FIG. 1, the primary medication bag 40 of FIG. 2 includes an integral (as opposed to discrete) flow control means and drip chamber 50 and 52, the details of which will be described in greater detail hereinafter. Moreover, the main IV fluid line 48 includes a unique, quick-disconnect fluid coupler 54, the details of which will also soon be described, by which to quickly and easily interconnect the main fluid line 48 with the drip chamber 52 of primary medication bag 40 so that a carefully regulated and reliably controlled volume of fluid can be supplied from bladder 44 to catheter assembly 46.

The safety IV system of FIG. 2 also includes a plurality of secondary medication bags 56-58, each containing a respective fluid filled bladder 60-62, integral flow control means 64-66, and integral drip chambers 68-70. Secondary fluid lines 72-74 include the aforementioned quick-disconnect fluid coupler 54 molded onto opposite ends thereof so that said secondary fluid lines may be interconnected between drip chambers 68-70 of respective secondary medication bags 56-58 and the main IV fluid line 48. That is, and as will be described in greater detail when referring to FIG. 3, by virtue of fluid coupler 54, the secondary fluid lines 72-74 are quickly and easily connected in fluid communication with main IV fluid line 48 through an efficient array of fluid tubes that are integrally molded into the platen appendage 43 of primary medication bag 40, whereby the Y-connectors and long secondary fluid lines common to the conventional IV system of FIG. 1 are eliminated.

Figure 4:
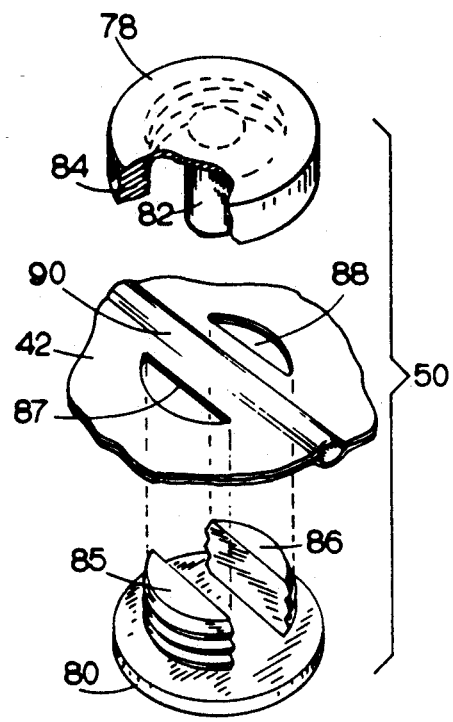
FIG. 4 is an exploded view of the flow control device from the fluid medication bag shown in FIG. 3.
Figure 5:
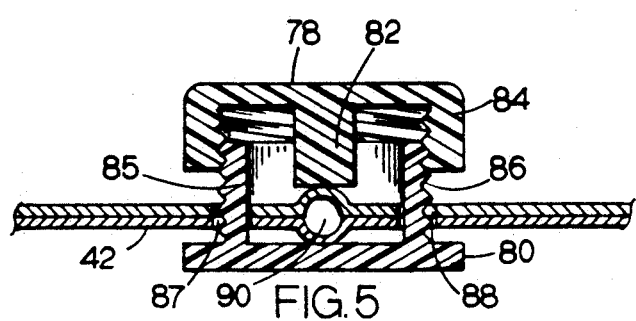
FIG. 5 is a cross-section taken along lines 5—5 of FIG. 3.

Details of the flow control means 50 and drip chamber 52 which are integral to the medication bag 40 of the safety IV system of the present invention are now described According to the preferred embodiment of the invention and referring concurrently to FIGS. 3-5 of the drawings, flow control means 50 includes a pressure regulating knob 78 and an oppositely disposed pressure regulating base 80. The pressure regulating knob 78 includes a downwardly extending pressure inducing stem 82 of solid cross section. Pressure regulating knob 78 also includes a screw threaded peripheral lip 84 extending downwardly therefrom to surround stem 82. Projecting upwardly from the pressure regulating base 80 of flow control means 50 is a pair of spaced, arcuate shaped screw threaded locating elements 85 and 86.

In the assembled relationship of FIG. 5, the arcuate shaped locating elements 85 and 86 of base 80 extend through corresponding arcuate shaped slots 87 and 88 formed in the flexible platen 42 of medication bag 40. As is best shown in FIG. 4, slots 87 and 88 are formed through platen 42 at opposite sides of a proximal drip chamber lumen 90 which extends between and communicates fluidically with bladder 44 and drip chamber 52. Accordingly, the screw threaded locating elements 85 and 86 from the base 80 of flow control means 50 are received within and mated to the screw threaded peripheral lip 84 of knob 78 with the proximal drip chamber lumen 90 being received in the space between locating elements 85 and 86 and positioned immediately below stem 82.

In operation, a clockwise rotation of the pressure regulating knob 78 of flow control means 50 relative to the pressure regulating base 80 causes a corresponding movement of the pressure inducing stem 80 towards and into contact with drip chamber lumen 90 so as to compress said lumen. That is to say, as knob 78 is rotated in the clockwise direction, lumen 90 is compressed by stem 82 from a fully open to a completely closed cross section, whereby to regulate the rate at which fluid flows from bladder 44 to main IV fluid line 48 via said lumen. To this end, the platen 42 of medication bag 40 contains printed indicia or calibration markings (best shown in FIG. 3) by which to indicate different positions to which pressure regulating knob 78 can be rotated for successively increasing the compressive force applied by stem 82 to lumen 90. As the compressive force increases, the cross sectional flow area of lumen 90 is correspondingly decreased from a first position of pressure regulating knob 78 (designated "3") where the flow rate through lumen 90 is maximized to a last position of knob 78 (designated OFF) at which fluid flow through lumen 90 is completely blocked.

By virtue of flow control means 50, a health care worker will be able to precisely regulate the rate at which fluid flows through proximal drip chamber lumen 90 from bladder 44. Of course, a counter-clockwise rotation of pressure regulating knob 78 relative to pressure regulating base 80 will increase the cross sectional flow area of lumen 90 and thereby increase the rate at which fluid flows from bladder 44 until lumen 90 is fully open and the flow rate therethrough is, once again, maximized.

The drip chamber 52 of medication bag 40 includes a hollow body having spaced, parallel aligned support grooves extending therearound (best shown in FIG. 3). Drip chamber 52 is integrally molded into the platen 42 of medication bag 40 between the proximal drip chamber lumen 90 and a distal drip chamber lumen 92 so as to efficiently regulate the rate at which fluid is delivered from bladder 44 to main IV fluid line 48.

Figure 6:
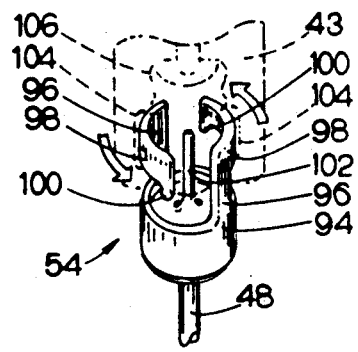
FIG. 6 illustrates a unique quick-disconnect fluid coupler by which fluid lines of the IV system of FIG. 2 may be efficiently interconnected.

The one piece, quick-disconnect fluid coupler 54 is best described while referring to FIGS. 3 and 6 of the drawings. Fluid coupler 54 is preferably injection molded from a relatively rigid plastic material and includes a generally hollow body 94 that is open at one end and substantially closed at the opposite end. Extending upwardly from the coupler body 94 is a pair of spaced, parallel aligned arms 96. Each arm 96 terminates with a arcuate, perpendicularly projecting locking finger 98 and a downwardly extending locking flange 100. Projecting upwardly from the closed end of coupler body 94 and coaxially aligned with the arcuately shaped locking fingers 98 thereof is a hollow fluid cannula 102. One end of the main IV fluid line 48 is integrally connected (e.g. molded) to cannula 102 through the closed end of coupler body 94 so that a continuous fluid path can be established from fluid coupler 54, at cannula 102, to the IV catheter assembly (designated 46 in FIG. 2) by way of main IV fluid line 48.

A pair of spaced, parallel aligned locking perforations 104 are formed through platen appendage 43. Distal drip chamber lumen 92 communicates fluidically with a hollow cannula receptacle 106 that is molded into platen appendage 43. Cannula receptacle 106 includes an elastomeric sleeve 108 which is heat sealed therewithin so as to receive the cannula 102 of fluid coupler 54 to thereby enhance the fluid transfer efficiency between said coupler and cannula receptacle 106.

In operation, fluid coupler 54 is removably connected to the cannula receptacle 106 of medication bag 40 to complete a fluid path between bladder 44 and main IV fluid line 48 (via proximal drip chamber lumen 90, drip chamber 52 and distal drip chamber lumen 92). More particularly, the cannula 102 of fluid coupler 54 is inserted into the elastomeric sleeve 108 of cannula receptacle 106, and the arms 96 of coupler 54 are rotated (in the direction of the reference arrows of FIG. 6), such that locking fingers 98 are received through respective locking perforations 104 in the platen appendage 43. With the fingers 98 of coupler 54 located through perforations 104 and cannula 102 received within elastomeric sleeve 108, the locking flanges 100 of fingers 98 project downwardly relative to the perforations 104 to block an inadvertent counter-rotation of said fingers and a removal of cannula 102 from cannula receptacle 106. However, by simply lifting upwardly on the body 94 of coupler 54, the locking flanges 100 may be aligned with locking perforations 104 to permit locking fingers 98 to be rotated out of the perforations 104 in platen appendage 43, whereby cannula 102 can be removed from the elastomeric sleeve 108 of cannula receptacle 106 by which fluid coupler 54 is quickly disconnected from the medication bag 40.

As is best shown in FIG. 3 and as was previously described when referring to FIG. 2, any suitable number of cannula receptacles 106 can be integrally molded into the platen appendage 43 of primary medication bag 40. Each cannula receptacle 106 includes a respective fluid tube which is interconnected with either distal drip chamber lumen 92 (as shown) or with proximal drip chamber lumen 90. Thus, the fluid medication from a plurality of secondary medication bags (designated 56-58 in FIG. 2) may be conveniently delivered to the main IV fluid line 48 by merely connecting the fluid couplers 54 associated with the secondary fluid lines (designated 72-74 in FIG. 2) to the elastomeric sleeves 108 of corresponding cannula receptacles 106 at the platen appendage 43 of primary medication bag 40. By virtue of the quick disconnect nature of the fluid coupler 54 and cannula receptacle 106 described herein, a compact IV system is available which may be easily assembled with less likelihood that the associated array of fluid tubing might become tangled or hooked onto the surroundings in the event that the primary medication bag 40 is moved.

A self-adhering identification strip 110 is located on the platen 42 of medication bag 40. Strip 110 includes a tear-off portion 111 which may be removed from platen 42 and adhesively affixed around the body of an associated fluid coupler 54 (best shown in FIG. 24). By printing suitable indicia on the identification strip 110 and its tear-off portion 111, health care workers will have a reliable way to verify the interconnection of the fluid lines from the medication bags of the IV system and thereby assure that intended medication from each bag is being delivered at a proper location within the system.

Figure 7:
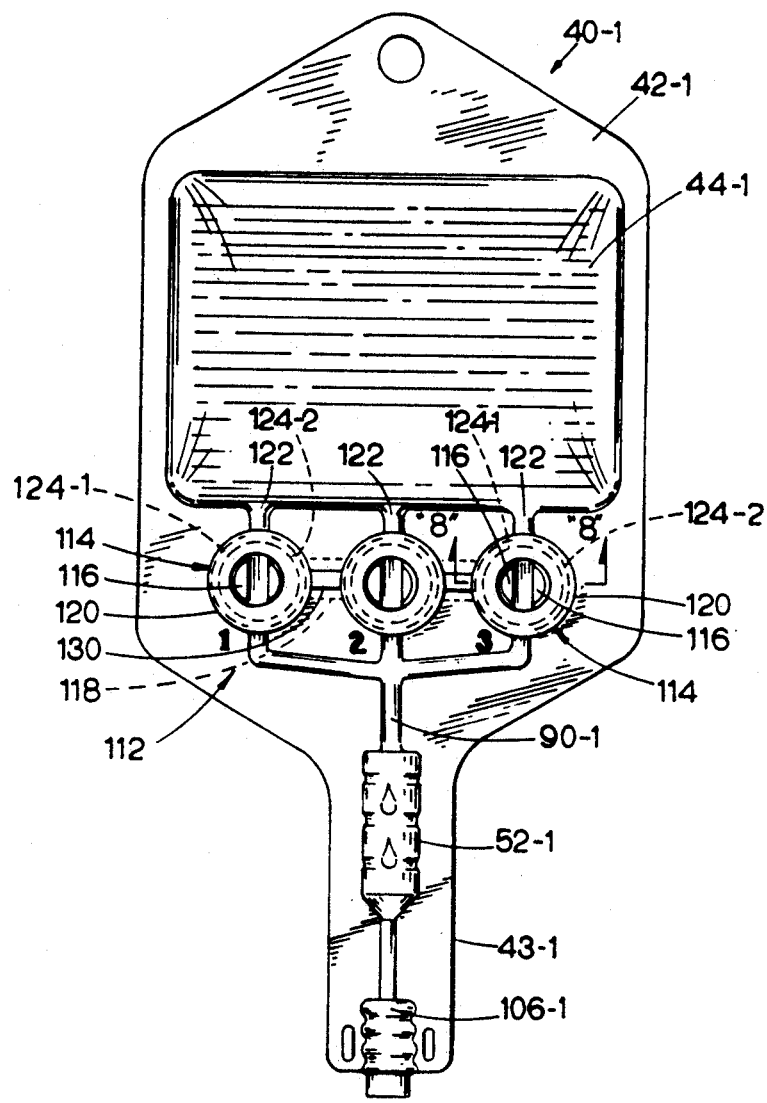
FIG. 7 shows a fluid medication bag having a fluid flow control device that is formed in accordance with an alternate embodiment of the present invention.
Figure 8:
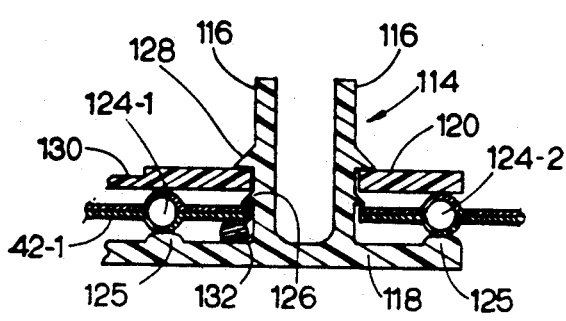
FIG. 8 is a cross-section taken along lines 8—8 of FIG. 7.
Figure 9:
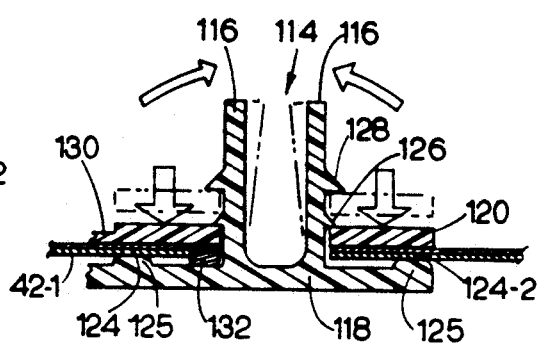
FIG. 9 shows the flow control device of FIG. 8 in a locked condition to prevent fluid flow.

FIGS. 7-9 of the drawings illustrate fluid flow control means 112 that is formed in accordance with an alternate embodiment of the present invention. Like the flow control means 50 of FIGS. 3-5, flow control means 112 is integral to a flexible medication bag 40-1 and is located between the fluid filled bladder 44-1 of said bag 40-1 and a proximal drip chamber lumen 90-1 of drip chamber 52-1 so as to accurately regulate the rate at which fluid flows from bladder 44-1 into drip chamber 52-1. The flow control means 112 of FIGS. 7-9 includes a plurality of (e.g. three) identical flow control devices 114 that are associated with respective fluid tubes 122. Therefore, only a single flow control device 114 will now be described.

Flow control device 114 includes a pair of outwardly extending, parallel aligned pressure release hubs 116 that are integrally connected to and supported by a relatively rigid bottom pressure control plate 118. Bottom pressure control plate 118 is common to the hubs 116 from each of the plurality of flow control devices 114. Spaced above the bottom pressure control plate 118 so as to surround respective pairs of hubs 116 are a plurality of pressure control discs 120. The pressure control discs 120 of flow control means 112 are spaced axially from and interconnected with one another by means of a relatively narrow, flexible strip 130. By virtue of the flexible strip 130, selective ones of the pressure control discs 120 may be depressed by a health care worker and moved towards the bottom pressure control plate 118 for an advantage that will soon be described.

Fluid tubes 122 extend from bladder 44-1 to communicate with proximal drip chamber lumen 90-1 at a common fluid connection therewith. Each fluid tube 122 is bifurcated into a pair of fluid paths 124-1 and 124-2 at each of the flow control devices 114. More particularly, the bifurcated fluid paths 124-1 and 124-2 are of semicircular configuration and extend between the bottom plate 118 and top disc 120 of each flow control device 114. A pair of raised locating nubs 125 extend upwardly from bottom pressure control plate 118 to receive respective bifurcated fluid paths 124-1 and 124-2. As will soon be described, the pressure control disc 120 can be moved towards and locked against the bottom pressure control plate 118 to compress fluid paths 124-1 and 124-2 and thereby control the rate at which fluid flows from bladder 44-1 to drip chamber 52-1.

Each pressure release hub 116 includes a radially outward extending lower locking detent 126 and a radially outwardly extending upper locking detent 128. In the unlocked condition of FIG. 8, pressure control disc 120 is spaced above bottom control plate 118 and retained between the lower and upper locking detents 126 and 128 of pressure release hubs 116. At the same time that the lower plate and upper disc 118 and 120 are spaced from one another, each of the bifurcated fluid paths 124-1 and 124-2 are open so that fluid may be delivered from bladder 44-1 to proximal drip chamber lumen 90-1 at the maximum flow rate.

In FIG. 9, a downward pushing force is manually applied to the pressure control disc 120, whereby to advance disc 120 from the unlocked condition (shown in phantom) spaced above pressure control plate 118 to the locked condition adjacent said plate 118. The pressure control disc 120 is retained by lower locking detent 126 in close proximity to the pressure control plate 118 such that each of the bifurcated fluid paths 124-1 and 124-2 of fluid tube 122 is compressed between top disc 120 and the locating nubs 125 of bottom plate 118, whereby the cross sectional flow area of fluid paths 124-1 and 124-2 is reduced to zero. Therefore, it may be appreciated that fluid flow through a fluid tube 122 can be blocked between bladder 44-1 and proximal drip chamber lumen 90-1 by selectively locking the corresponding flow control device 114 of flow control means 112.

Should it be desirable to restore fluid flow through the previously compressed fluid paths 124-1 and 124-2 of fluid tube 122, equal and opposite forces are manually applied to the opposing pair of pressure release hubs 116 of fluid control device 114, whereby to cause said hubs to rotate towards one another. As hubs 116 are rotated together (shown in phantom in FIG. 9), the lower locking detents 126 are correspondingly moved out of engagement with the pressure control disc 120 so that disc 120 will automatically return to the unlocked condition of FIG. 8. For this purpose, it is preferable to make the upper locking detent 128 radially longer than lower locking detent 126 so that disc 120 will once again be retained in the unlocked condition between locking detents 126 and 128. What is more, a spring 132 may be located between lower plate 118 and upper disc 120 so as to bias disc 120 away from plate 118 and towards the unlocked condition of FIG. 8 when pressure release hubs 116 are rotated together to release said disc from the locked condition of FIG. 9.

By virtue of the foregoing fluid control means 112, any number of the fluid control devices 114 can be selectively manipulated so that four different flow rates may be achieved. That is to say, all of the flow control devices 114 may either be in the unlocked condition (whereby fluid paths 124-1 and 124-2 are open) as shown in FIG. 8 or the locked condition (whereby fluid paths 124-1 and 124-2 are closed) as shown in FIG. 9, so that fluid delivered to drip chamber 52-1 flows at either the maximum rate or at zero rate, respectively. Likewise, any one or any two of the flow control devices 114 may be selectively activated and locked to successively decrease the flow rate below that which is possible when all of the flow control devices 114 are unlocked and the fluid paths 124-1 and 124-2 are open.

As best shown in FIG. 7, a cannula receptacle 106-1 (similar to that described when referring to FIG. 3) is molded into the distal appendage 43-1 of platen 42-1 of medication bag 40-1 to permit a quick-disconnect fluid coupler (designated 54 in FIG. 6) to be mated thereto in a manner previously described so that fluid may be delivered from bladder 44-1 to an IV catheter (not shown) by way of the main IV fluid line (also not shown).

FIGS. 10-14 of the drawings illustrate a fluid flow control means 136 that is formed in accordance with another embodiment of the present invention. Flow control means 136 is integral to a flexible medication bag 40-2 and is adapted to permit a health care worker to selectively and accurately control the rate at which fluid flows from the fluid filled bladder 44-2 of bag 40-2 to a drip chamber 52-2 that is integrally molded into the supporting platen 42-2 of said medication bag. Flow control means 136 includes a flexible fluid tube 138 that is molded into the platen 42-2 of medication bag 40-2. The proximal end of tube 138 communicates with bladder 44-2 and the distal end of said tube communicates with drip chamber 52-2. A portion of fluid tube 138 between the proximal and distal ends thereof is curved. A V-shaped flow regulator 140 cooperates with and rotates relative to the curved portion of fluid tube 138 to selectively control the rate at which fluid flows therethrough.

Flow regulator 140 includes a pair of opposing flow control surfaces 142 between which the curved portion of fluid tube 138 is received. First ends of flow control surfaces 142 are joined together and extend through an opening formed in the platen 42-2, such that the flow control surfaces 142 are located at opposite sides of said platen. A pair of reinforcing rings 144 surrounds the opening at opposite sides of the platen 42-2 to provide support for the flow control surfaces 142 and permit flow regulator 140 to rotate relative to fluid tube 138.

As is best shown in FIG. 10, the platen 42-2 of medication bag 40-2 contains printed indicia or calibration markings by which to indicate different positions along curved fluid tube 138 to which flow regulator 140 can be rotated for increasing or decreasing the cross sectional flow area of tube 138 so as to accurately and selectively control the rate at which fluid flows from bladder 44-2 to drip chamber 52-2. To this end, it is important to note that, because of the progressively wider separation between the opposing flow control surfaces 142 of V-shaped flow regulator 140, the compressive force to which the curved fluid tube 138 is subjected between flow control surfaces 142 will vary depending upon the position to which regulator 140 is rotated relative to the tube 138.

More particularly, the flow regulator 140 can be located at a first position (designated OFF in FIG. 10) by which the curved fluid tube 138 is located closest to the intersection of opposing flow control surfaces 142 (best shown in FIG. 11). Because of the V-shaped configuration of flow regulator 140, the distance between the opposing flow control surfaces 142 is minimized at the OFF position of regulator 140, whereby the compressive force applied to fluid tube 138 by surfaces 140 is maximized so as to reduce the cross-sectional flow area of tube 138 to zero and thereby completely block the flow of fluid therethrough.

With the flow control regulator rotated to a second position (designated "1" in FIG. 10), the curved fluid tube 138 will be located forward of the intersection of opposing flow control surfaces 142 (best shown in FIG. 12). Hence, the compressive force applied to fluid tube 138 by opposing flow control surfaces 142 is reduced (relative to the OFF position of regulator 140) to increase the cross-sectional flow area of said tube 138 and thereby permit fluid to flow therethrough to drip chamber 52-2.

With the flow control regulator 140 rotated to a third position (designated "2" in FIG. 10), the curved fluid tube 138 will be located further from the intersection of opposing flow control surfaces 142 (best shown in FIG. 13). Hence, the compressive force applied to fluid tube 138 by flow control surfaces 142 is further reduced in the third position (relative to the second position of regulator 140) to still further increase the cross-sectional flow area of said tube 138 and, thereby, increase the rate at which fluid flows therethrough to drip chamber 52-2.

With the flow control regulator 140 rotated to a forth position (shown in phantom and designated "3" in FIG. 10), the curved fluid tube 138 will be located farthest away from the intersection of opposing flow control surfaces 142 such that the distance between said flow control surfaces 142 is maximized (best shown in FIG. 14). Accordingly, the compressive force applied to fluid tube 138 by flow control surfaces 142 is removed and the cross-sectional flow area of tube 138 is maximized, whereby to correspondingly maximize the rate at which fluid flows through said tube to drip chamber 52-2.

A total of four flow positions are illustrated in FIG. 10 to which flow regulator 140 can be selectively rotated to vary the flow rate through curved fluid tube 138 from zero (at the OFF position) to maximum (at the "3" position). However, the four positions illustrated are not to be regarded as a limitation of this embodiment, and any number of positions may be printed onto the platen 42-2 of medication bag 40-2. As will be apparent to those skilled in the art, by increasing the number of flow positions to which flow regulator 140 can be successively rotated, a health care worker will be provided with the ability to more accurately and controllably regulate the rate at which fluid flows between bladder 44-2 and the drip chamber 42-2. What is more, and as is best shown in FIG. 10, a previously described cannula receptacle 106-2 is molded into the distal appendage of platen 42-2 of medication bag 40-2 so that a quick disconnect fluid coupler (designated 54 in FIG. 6) may be mated thereto in order to deliver fluid from bladder 44-2 to an IV catheter by way of the main IV fluid line.

FIGS. 15-18 of the drawings illustrate a fluid flow control means 150 that is formed in accordance with yet another embodiment of the present invention. Flow control means 150 is integral to a flexible medication bag 40-3 and is adapted to permit a health care worker to selectively and accurately control the rate at which fluid flows from the fluid filled bladder 44-3 of bag 40-3 to a drip chamber 52-3 that is integrally molded into the supporting platen 42-3 of said medication bag. Flow control means 150 includes a plurality of (e.g. three) flexible fluid tubes 152, 153 and 154 that are molded into the platen 42-3 of medication bag 40-3. The proximal ends of tubes 152-154 communicate with bladder 44-3, and the distal ends of said tubes communicate with drip chamber 52-3 by way of a common proximal drip chamber lumen 90-3 that is also molded into platen 42-3. Each of the fluid tubes 152-154 extends between the bladder 44-3 and lumen 90-3 at a particular skewed (i.e. non parallel) alignment relative to one another for a purpose that will be described in greater detail hereinafter.

Figure 16:
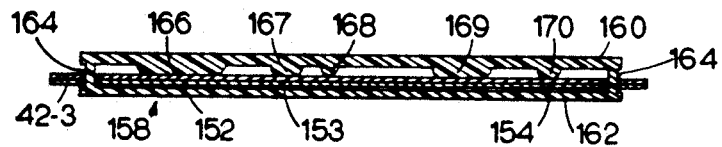
FIG. 16 is a cross-section taken along lines 16—16 of FIG. 15.

Flow control means 150 also includes a relatively flat flow control bar 158 which cooperates with and is slidable axially relative to the fluid tubes 152-154 so that the flow of fluid through said tubes can be selectively controlled. More particularly, and as is shown in FIG. 16, flow control bar 158 includes a top pressure control surface 160 and an opposing bottom support surface 162. The top and bottom surfaces 160 and 162 of flow control bar 158 are spaced from one another with the platen 42-3 of medication bag 40-3 located therebetween. Top and bottom surfaces 160 and 162 are integrally connected together through a pair of parallel aligned slots 164 that are formed in opposite sides of platen 42-3. The flow control bar 158 is attached to medication bag 40-3 so as to ride through slots 164. Accordingly, the top pressure control surface 160 of flow control bar 158 will slide over the front of platen 42-3 (in contact with the fluid tubes 152-154 that are molded therein), and the bottom support surface 162 of bar 158 will slide over the back of platen 42-3. As will soon be described, the rate of fluid flow from bladder 44-3 to drip chamber 52-3 is dependent upon the position of flow control bar 152 relative to fluid tubes 152-154.

Coextensively formed with and projecting inwardly from the top pressure control surface 160 of flow control bar 158 is a series of laterally spaced pressure bumps 166, 167, 168, 169 and 170. As an important detail of the present embodiment, the pressure pumps 166-170 are provided with particular sizes and locations along pressure control surface 160 so as to be adapted to engage respective ones of the fluid tubes 152-154 as flow control bar 158 moves axially over said tubes. That is to say, a pre-determined relationship exists between the location of the bumps 166-170 on the top pressure control surface 160 of flow control bar 158 and the location of the fluid tubes 152-154 in platen 42-3, whereby to control the fluid flow through said tubes depending upon the location of flow control bar 158 at platen 42-3 and the corresponding location of pressure bumps 166-170 relative to respective fluid tubes 152-154.

Figure 15:
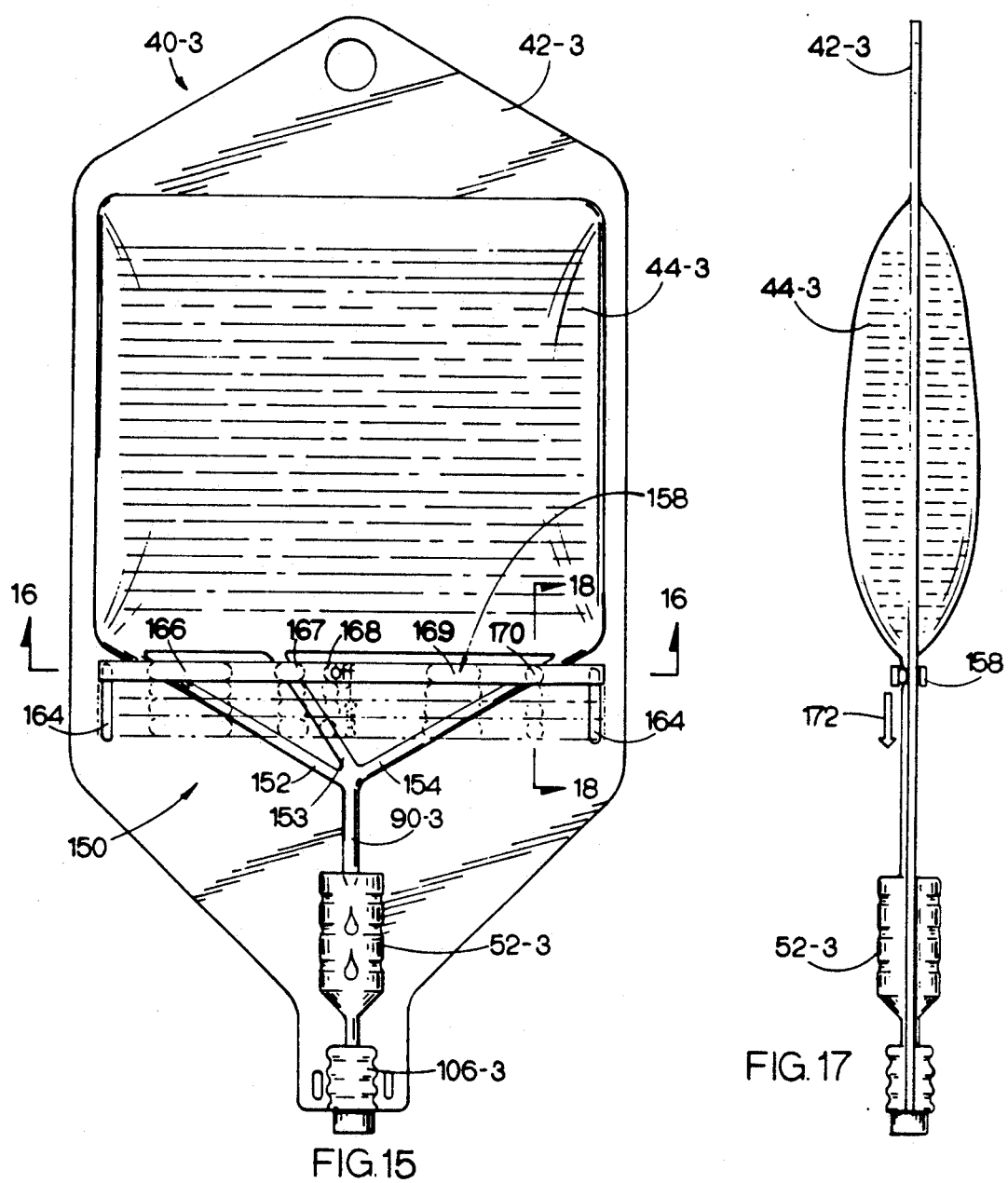
FIG. 15 shows a fluid medication bag having a fluid flow control device that is formed in accordance with yet another embodiment of the present invention.
Figures 17, 18:
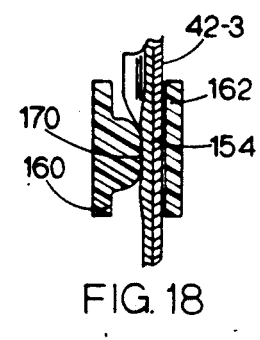
FIG. 17 is a side view of the medication bag of FIG. 15.
FIG. 18 is an enlargement of a detail illustrated in FIG. 17.

As is best shown in FIG. 15, the platen 42-3 of medication bag 40-3 contains printed indicia or calibration markings by which to indicate different positions along platen 42-3 to which flow control bar 158 can be moved (i.e. by sliding said bar 158 downwardly through slots 164 in the direction of the reference arrow 172 of FIG. 17) to either open or close all or some of fluid tubes 152-154 and thereby regulate the rate at which fluid flows via said tubes from bladder 44-3 to drip chamber 52-3. Flow control bar 158 is shown in FIG. 15 located at a first position on platen 42-3 (designated OFF) by which certain ones of the raised pressure bumps from the top pressure control surface 160 of bar 158 close each of the fluid tubes 152-154. That is, in the OFF position, pressure bump 166 engages and compresses fluid tube 152, bump 167 engages and compresses fluid tube 153, and bump 170 engages and compresses fluid tube 154 (best shown in FIG. 16). Accordingly, each fluid tube 152-154 of flow control means 150 is engaged and compressed by a respective raised pressure bump 166, 167 and 170 from the top pressure control surface 160 of flow control bar 158, such that the cross-sectional flow area of said tubes is reduced to zero and the flow of fluid through each of said tubes is completely blocked.

By moving flow control bar 158 downwardly through slots 164 to a second position along platen 42-3 (shown in phantom in FIG. 15 and designated "1"), fluid is permitted to flow from bladder 44-3 to drip chamber 52-3. That is, and in the second position, pressure bumps 166 and 167 will compress and close fluid tubes 152 and 153, respectively, whereby to block the flow of fluid therethrough. However, fluid tube 154 will now be open in the second position of flow control bar 158 to permit fluid to flow therethrough at a rate which is proportional to the cross-sectional flow area thereof.

By moving flow control bar 158 downwardly through slots 154 to a third position along platen 42-3 (shown in phantom in FIG. 15 and designated "3"), pressure bumps 166 and 169 will compress and close fluid tubes 152 and 154, respectively, whereby to block the flow of fluid therethrough. However, fluid tube 153 will now be open in the third position of flow control bar 158 to permit fluid to flow therethrough.

By moving flow control bar 158 downwardly through slots 164 to a forth position along platen 42-3 (shown in phantom in FIG. 15 and designated "3"), pressure bumps 168 and 169 will compress and close fluid tubes 153 and 154, respectively, to block the flow of fluid therethrough. However, fluid tube 152 will now be open in the fourth position of flow control bar 158 to permit fluid to flow therethrough.

It is to be understood that the fluid flow control device 150 of this embodiment could be formed to include more than the four flow control positions shown in FIG. 15. Thus, any two or all three of the fluid tubes 152-154 could be selectively opened to increase the rate at which fluid flows between bladder 44-3 and drip chamber 52-3. Moreover, the diameter of fluid tubes 152-154 (and the corresponding cross-sectional flow areas thereof) may vary relative to one another so as to achieve successively increasing flow rates in the second, third and forth positions of flow control bar 158. Whats more, it should be apparent that the flow control bar 158 can also be moved upwardly along platen 42-3 (in an opposite direction to that indicated by reference arrow 172 in FIG. 17) when it is desirable to decrease or block the flow of fluid from bladder 44-3 to drip chamber 52-3. What is still more, and as is best shown in FIG. 15, a previously described cannula receptacle 106-3 is molded into the distal appendage of the platen 42-3 of medication bag 40-3 so that a quick-disconnect fluid coupler (designated 54 in FIG. 6) may be mated thereto so that fluid can be delivered from bladder 44-3 to an IV catheter by way of the main IV fluid line.

FIGS. 19-21 of the drawings illustrate a fluid flow control means 176 that is formed in accordance with a further embodiment of the present invention. Flow control means 176 is integral to a flexible medication bag 40-4 and is adapted to permit a health care worker to selectively and accurately control the rate at which fluid flows from the fluid filled bladder 44-4 of a bag 40-4 to a drip chamber 52-4 that is integrally molded into the supporting platen 42-4 of said medication bag. Flow control means 176 includes a plurality of (e.g. three) flexible fluid tubes 178, 179 and 180 that are molded into the platen 42-4 of medication bag 40-4. The proximal ends of fluid tubes 178-180 communicate with bladder 44-4, and the distal ends of said tubes communicate with drip chamber 52-4 by way of a common proximal drip chamber lumen 90-4 which is also molded into platen 42-4. Drip chamber lumen 52-4 communicates with a previously described cannula receptacle 106-4 by way of a distal drip chamber lumen 92-4.

Each of the fluid tubes 178-180 includes a curved (e.g. semi-circular) portion 182, 183 and 184, the advantage of which will soon be described. The curved portions 182-184 of fluid tubes 178-180 are interfaced with respective pressure control flaps 186 that permit a health care worker to selectively open or close said fluid tubes to the flow of fluid therethrough. First ends of pressure control flaps 186 are received within respective openings 190 that are formed through the platen 42-4 of medication bag 40-4. The opposite ends of the pressure control flaps 186 are integrally and pivotally connected to the platen 42-4, such that said flaps are rotatable from a first position (shown in FIGS. 19 and 20), lying flat within the openings 190 of said platen at which each of the fluid tubes 178-180 is open to permit maximum fluid flow, to a second position (shown in FIG. 21) at which said flaps 186 are removed from openings 190 and folded tightly around respective fluid tubes 178-180, whereby said tubes will be compressed and closed to the flow of fluid therethrough.

Flow control means 176 also includes pairs of complementary fasteners by which to releasably secure one or more of the pressure control flaps 186 in the aforementioned folded position around respective fluid tubes 178-180. More particularly, a female catch 192 is affixed to each pressure control flap 186 at one side of curved tubes 182-184, and a male snap 194 is affixed to platen 42-4 at the opposite side of curved tubes 178-180 Thus, when it is desirable to block the flow through a particular one of the fluid tubes 178-180, a health care worker rotates the corresponding pressure control flap 186 out of its opening 190 in platen 42-4 and folds said flap tightly around the curved portion (e.g. 184) of the particular fluid tube (e.g. 180), the flow through which is to be controlled. As is best shown in FIG. 21, the female catch 192 of pressure control flap 186 is connected to the male snap 194 of platen 42-4, whereby to releasably retain the flap 186 in its folded configuration around the fluid tube 180 to thereby compress the curved portion 184 and reduce the cross-sectional flow area to zero so as to completely block the flow of fluid therethrough. By providing fluid tube 180 with a curved portion 184 around which pressure control flap 186 may be folded, both the pressure generated by flap 186 and the compressive force applied to said curved portion can be maximized, whereby to reliably block the flow of fluid through tube 180.

It should be apparent that the pressure control flaps 186 associated with some, all or none of the fluid tubes 178-180 may be rotated and releasably retained in the folded configuration of FIG. 21. Moreover, the diameters (i.e. cross-sectional areas) of the tubes 178-180 may vary relative to one another to permit the health care worker greater control in selectively and accurately regulating the rate at which fluid flows from bladder 44-4 into the drip chamber 52-4 of medication bag 40-4.

Figure 22:
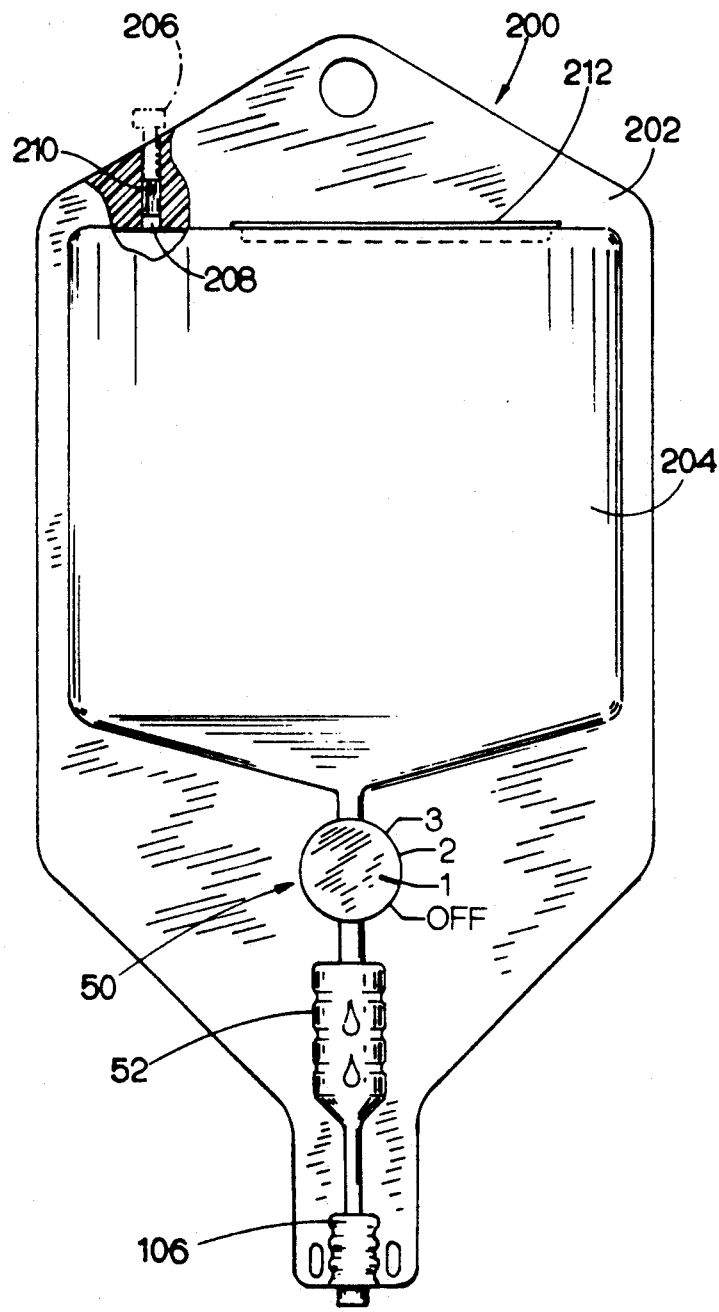
FIG. 22 shows a relatively rigid fluid medication bag that may be substituted for the medication bag of FIG. 3.
Figure 23:
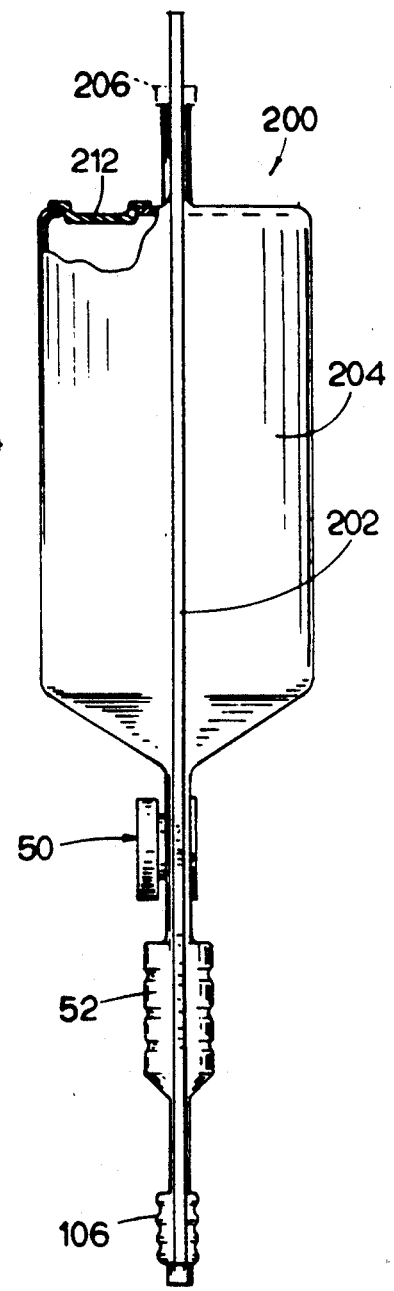
FIG. 23 is a side view of the medication bag of FIG. 22.

The medication bags which have been described above when referring to FIGS. 1-21 are characterized by a relatively flexible platen which surrounds and provides support for a flexible fluid filled bladder. Accordingly, the flexible bladder of these previously described medication bags collapses under atmospheric pressure to force fluid outwardly therefrom for delivery to an integral drip chamber. FIGS. 22 and 23 of the drawings illustrates a medication bag 200 which includes a hard plastic platen 202 to surround and support a relatively rigid, fluid filled compartment 204. Because of its rigid, inflexible construction, fluid compartment 204 will not collapse under atmospheric pressure as fluid drains therefrom. Therefore, in order to cause fluid to flow outwardly from compartment 204, medication bag 200 is provided with a hollow vent 208 in which a removable plug 206 is located. Vent 208 extends through platen 202 and communicates with the interior of fluid filled compartment 204. A filter 210 may be located within vent 208 to preserve the sterility of the fluid within compartment 204. Thus, when the plug 206 is removed from vent 208, filtered air from the surrounding atmosphere will have a path through which to fill compartment 204 and displace the fluid which is originally stored therein.

Medication bag 200 is also provided with a suitable flow control means to enable a health care worker to selectively control the rate at which fluid flows from compartment 204 to the drip chamber. For purposes of illustration, only, the flow control means 50 which was previously disclosed when referring to FIGS. 3-5 is shown carried by platen 202 and located between fluid compartment 204 and drip chamber 52. Moreover, the drip chamber 52 and a cannula receptacle 106, with which drip chamber 52 communicates, may be integrally molded into the platen 202 of medication bag 200 and used in a manner that was previously described when referring to FIG. 3.

A removable lid 212 is snap fit into an opening at the top of the rigid fluid compartment 204. Lid 212 can be removed from compartment 204 should it be desirable to refill said compartment with fluid. In the alternative, the lid 212 can be removed so that disposable IV system components may be safely stored within compartment 204 after the fluid has been drained therefrom. In this case, the empty fluid compartment serves as a Sharp's container to permit disposable medical debris to be safely handled and discarded within an enclosed housing.

In FIGS. 2 and 3 of the drawings, a compact, efficient IV system was shown including a primary medication bag 40 and a plurality of secondary medication bags (designated 56-58 in FIG. 2) that are fluidically connected to medication bag 40 by means of the attachment of quick disconnect fluid couplers 54 associated with each of the secondary medication bags to respective receptacles 106 molded into the platen 42 of primary medication bag 40. However, the multi-receptacle platen 42 of FIGS. 2 and 3 may be replaced by the multi-receptacle manifold 216 illustrated in FIG. 24 of the drawings. That is to say, instead of connecting the fluid couplers 54 from secondary medication bags to receptacles molded into platen 42, the fluid couplers may otherwise be connected through respective elastomeric gaskets which normally seal the ends of fluid tubes that are molded into the manifold 216.

More particularly, manifold 216 includes a common fluid tube 218. One end of common fluid tube 218 is sized to receive a section of a main IV fluid line 220 which communicates with the primary medication bag. The opposite end of common fluid tube 218 has an elastomeric gasket 221 sealed thereacross. A plurality of (e.g. three) secondary fluid tubes 222-1, 222-2 and 222-3 are connected at first ends thereof in fluid communication with common fluid tube 218. The opposite ends of secondary fluid tubes 222-1, 222-2 and 222-3 are sealed by elastomeric gaskets (designated 221 in FIG. 25). Surrounding and supporting the common and secondary fluid tubes is a relatively rigid, molded plastic manifold plate 224. Pairs of locking perforations 226 are formed through manifold plate 224 adjacent the normally sealed ends of each of the fluid tubes thereof. Locking perforations 226 perform the same function as the perforations 104 previously described when referring to FIGS. 3 and 6. Therefore, a fluid coupler 54 associated with the IV catheter assembly can be fluidically connected at the sealing gasket 221 of the common fluid tube 218 and fluid couplers 54-1, 54-2 and 54-3 associated with the secondary fluid lines 72-74 of respective secondary medication bags (designated 56-58 in FIG. 2) can be fluidically connected at the sealing gaskets of the secondary fluid tubes 221-1, 222-2, and 222-3.

By way of example, FIG. 25 illustrates the connection of the quick-disconnect fluid coupler 54-1 associated with secondary fluid line 72 to the sealing gasket 221 affixed to the secondary fluid tube 222-1 of manifold 216 so that fluid from a secondary medication bag (56 in FIG. 2) can be supplied to the IV catheter assembly via common fluid tube 218. That is, the locking fingers 98-1 of coupler 54-1 are rotated through respective locking perforations 226 at manifold plate 224, and the fluid cannula 102-1 is received at the interior of fluid tube 222-1 through sealing gasket 221.

FIGS. 26-31 of the drawings illustrate a preferred embodiment for the safety IV catheter assembly 46 which, as is shown in the IV system of FIG. 2, includes means by which to make a veni puncture through the patient's tissue so that fluid supplied to assembly 46 by way of the main IV fluid line 48 can be delivered to the patient. As shown in the as-packaged configuration of FIG. 26, catheter assembly 46 includes a hollow, tubular body 228 that is preferably formed from a soft, flexible material, such as vinyl, or the like. Catheter assembly 46 also includes a trocar 230 of solid cross section having a sharp tip by which to penetrate the patient's tissue. The sharp tip of trocar 230 is surrounded by a removable shield 232 to prevent an accidental needle stick at the loss of sterility. A trocar wire 234 extends longitudinally through the tubular body 228 of catheter assembly 46 so as to enable the trocar 230 to be removed from assembly 46 in a manner that will be described in greater detail hereinafter. The trocar wire 234, which is characterized by a relatively narrow diameter relative to trocar 230, is bonded at one end thereof to trocar 230 and at the opposite end to a manually accessible terminal cap 238.

Coaxially aligned with and surrounding trocar 230 at the distal end of catheter assembly 46 is a flexible (e.g. polymer) catheter cannula 240. Catheter cannula 240 communicates fluidically with the tubular body 228 of catheter assembly 46 so that fluid from the primary and secondary medication bags can be delivered to the patient after the trocar 230 first makes a veni puncture and then is removed from assembly 46. To this end, a disposable safety housing 242, into which trocar 230 can be withdrawn, is detachably connected to the proximal end of catheter assembly 46. A hollow receptacle 244 is attached (e.g. glued) to one end of safety housing 242 within which the proximal end of catheter assembly 46 is removably received. By way of example, the hollow receptacle 244 may have a flexible, expansible body, such as that common to a well-known bellows. A gasket 246, formed from a self-sealing elastomeric material, is positioned across the proximal end of catheter assembly 46 and sized to be received in a snap-fit engagement with the receptacle 244 of safety housing 242.

A gripping head 248 having suitable finger gripping grooves extending therearound is attached (e.g. glued) to the end of safety housing 242 opposite that at which receptacle 244 is located. Gripping head 248 includes a recessed pocket 250 formed therein which, as is best shown in FIG. 27, is aligned at an angle (designated $\theta$) with respect to a longitudinal axis of catheter assembly 46. A narrow channel 252 is axially aligned and communicates with pocket 250. Located at the interface of pocket 250 and channel 252 is an elastomeric trocar guide 254. The advantage of aligning pocket 250 and channel 252 at an angle (relative to the longitudinal axis of catheter assembly 46) and the purpose of trocar guide 254 will be disclosed in greater detail when referring to FIGS. 28-30. Nevertheless, in the as-packaged configuration of FIG. 26, the trocar wire 234 extends through catheter assembly 46 between trocar 230 and terminal cap 238 via tubular body 228, gasket 246 and the receptacle 244, pocket 250 and channel 252 of detachable safety housing 242.

Catheter assembly 46 also includes a pair of flexible stabilizing wings 256 which extend outwardly and in opposite directions from the tubular body 228 of said assembly. The wings 256 provide stabilization for catheter assembly 46 and prevent a premature removal of the catheter cannula 240 from the vein of the patient. A hollow push-in port 258 communicates fluidically with tubular body 228 so that additional supplies of medication may be delivered to the patient from a conventional syringe, or the like, by way of cannula 240. Push-in port 258 is closed in the as-packaged configuration by means of a needle penetrable elastomeric seal 260. The proximal end of catheter assembly 46 terminates at a relatively wide terminal plate 261. A pair of parallel aligned locking perforations 262 are formed through terminal plate 261, whereby the tubular body 228 of catheter assembly 46 can be coupled to the main IV fluid line after trocar 230 has been withdrawn to safety housing 242 and said safety housing has been detached from assembly 46 (best shown in FIG. 31).

Figure 28:
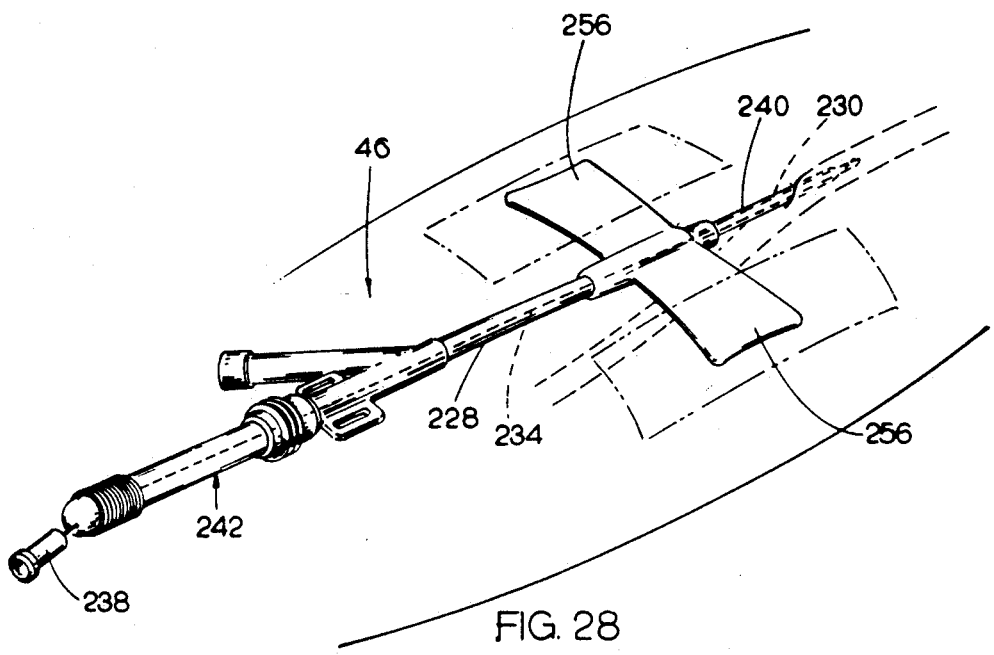
FIGS. 28-31 illustrate the operation of the safety IV catheter assembly of FIG. 27.

The operation of the safety catheter assembly 46 is now described while referring to FIGS. 28-31 of the drawings. In FIG. 28, the sharp trocar 230 has made a veni puncture through the patient's tissue and the catheter cannula 240 is located within the patient's vein. The outwardly extending wings 256 are taped to the patient's skin to prevent the removal of cannula 240. As previously described, the safety housing 242 is detachably connected at the proximal end of catheter assembly 46, and trocar wire 234 extends continuously from trocar 230 to terminal cap 238 via the tubular body 238 of assembly 46 and safety housing 242.

Figure 29:
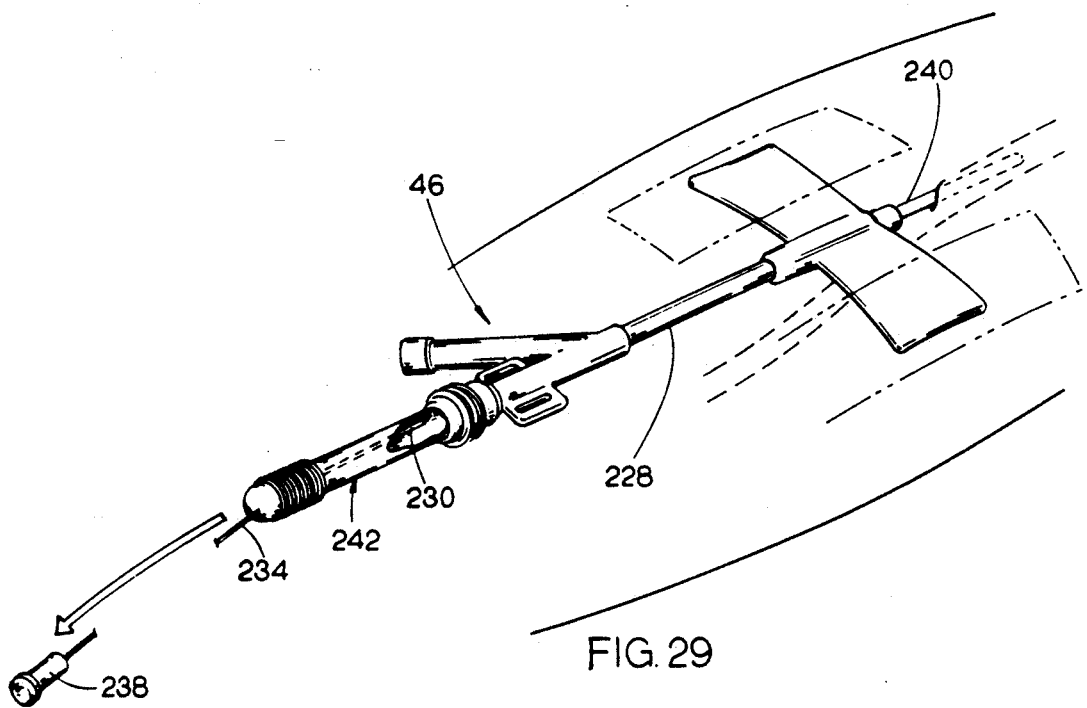

In FIG. 29, the trocar 230 is removed from the patient's tissue and withdrawn into the safety housing 242. More particularly, and referring concurrently to FIGS. 26, 27 and 29, after the veni puncture is made and the cannula 240 properly located, the terminal cap 238 is pulled in a proximal direction (as indicated by the reference arrow of FIG. 29). Inasmuch as trocar 230 is connected to terminal cap 238 by trocar wire 234, a proximal pulling force applied to terminal cap 238 causes a corresponding proximal relocation of trocar 230 through catheter assembly 46. That is, trocar 230 is pulled proximally through tubular body 228 and gasket 246 for receipt within the safety housing 242.

As is best shown in FIG. 27, the proximal pulling force is applied to terminal cap 238 until the trocar 230 (shown in phantom) is withdrawn from the distal end of catheter assembly 46 and received within the recessed pocket 250 formed in the gripping head 248 of safety housing 242. The narrow channel 252, which communicates with pocket 250, is sized to permit the relatively thin trocar wire 234 to be pulled therethrough. However, the size (i.e. diameter) of channel 252 is selected so as to be too small to permit the relatively thick trocar 230 to pass therethrough, such that trocar 230 will be captured within pocket 250.

The angled alignment of pocket 250 will inhibit the trocar 230 from being pushed distally through catheter assembly 46 after trocar 230 has been pulled proximally into safety housing 242. That is, the angled orientation of pocket 250 and the inclusion of trocar guide 254 therewithin will cause trocar 230 to be canted towards the side of safety housing 242 and out of alignment with the tubular body 228 of catheter assembly 46. Moreover, safety housing 242 may be provided with an inwardly flared forward end (best shown in FIG. 26) to further reduce the ability of trocar 230 to be inadvertently returned to the as-packaged configuration at the distal end of assembly 46.

Figure 30:
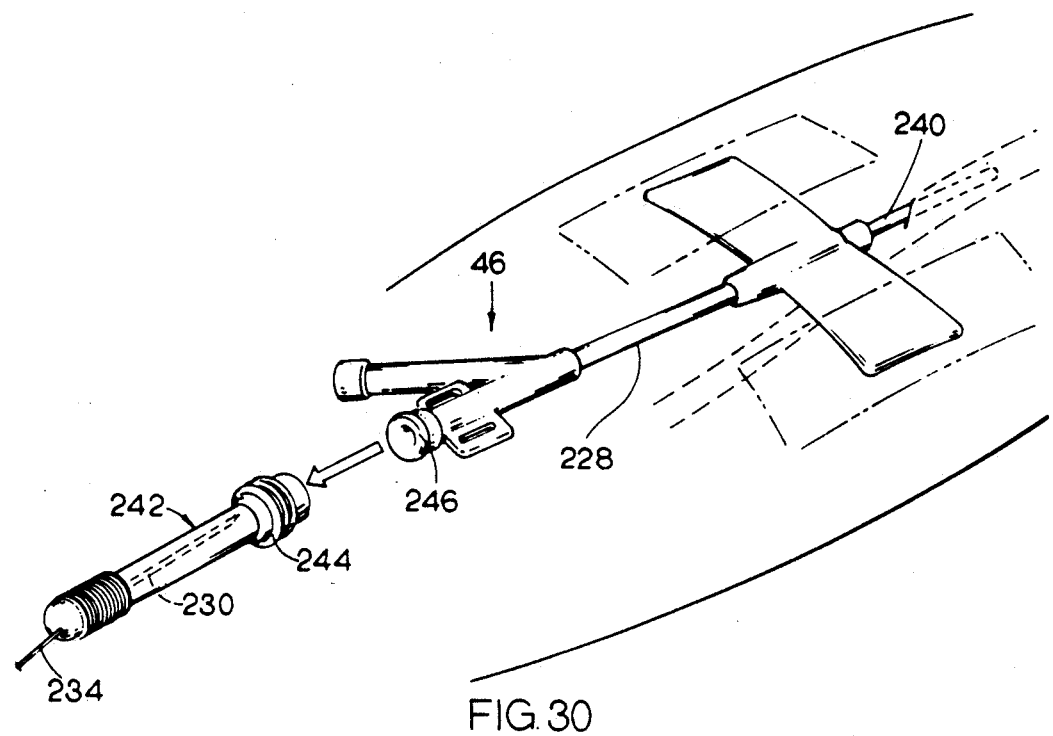

In FIG. 30, the safety housing 242 is detached from the proximal end of catheter assembly 46 to be discarded with the trocar 230 safely shielded and rendered inacessible therewithin so as to prevent an accidental needle stick and the possible spread of infectious disease. More particularly, by applying a proximal pulling force to safety housing 242 (in the direction of the reference arrow of FIG. 30), the extensible receptacle 244 thereof (best shown in FIG. 26) can be expanded and then snapped out of engagement with the gasket 246 that is sealed across the proximal end of assembly 46. Safety housing 242 advantageously eliminates the need to handle the trocar 230 and shields health care workers and other patients from exposure to possibly contaminated blood, as might otherwise occur if the trocar were to be pulled out of the catheter assembly in an unshielded condition, as is common to conventional IV systems.

When safety housing 242 is detached from catheter assembly 46, the aforementioned elastomeric gasket 246 performs the important function of interrupting flood flashback. That is to say, the self-sealing characteristic of gasket 246 will automatically close the puncture wound that is formed therein when the trocar wire 234 and trocar 230 are pulled through said gasket. Hence, any blood which rushes from the patient's vein through catheter cannula 240 and flexible body 228 will be blocked at the proximal end of catheter assembly 46 by gasket 246 so as to prevent health care workers and other patients from being exposed to possibly contaminated blood, another problem that is common to conventional IV systems.

Figure 31:
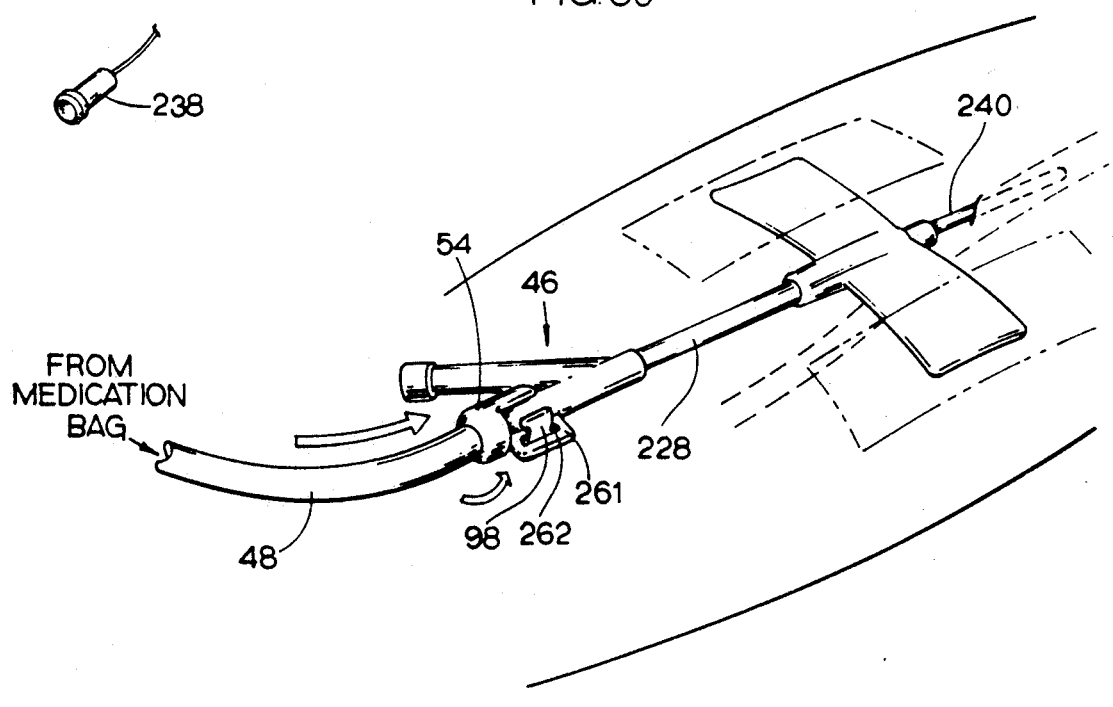

In FIG. 31, a fluid tube (e.g. the main IV fluid line 48 of FIG. 2) is connected to catheter assembly 46 to complete a fluid path from one or more medication bags to the catheter cannula 240. Fluid tube 48 includes a quick-disconnect fluid coupler 54, such as that which was previously disclosed when fingers 98 that are rotated through respective locking perforations 262 formed in the terminal plate 261 at the proximal end of assembly 46. Coupler 54 also has a fluid cannula (102 in FIG. 6) that is inserted through the previously described elastomeric gasket (246 in FIG. 26) so as to communicate fluidically with the tubular body 228 of catheter assembly 46.

Figures 32, 33:
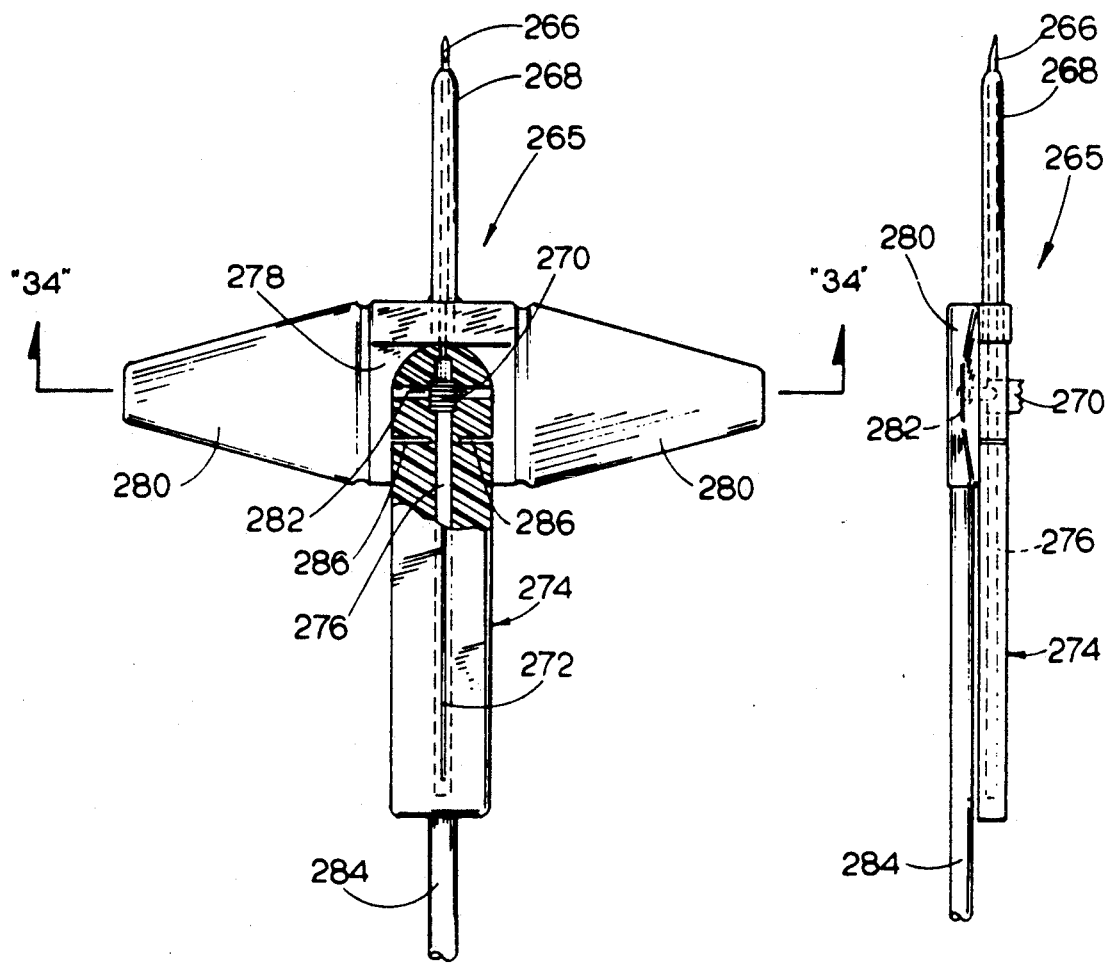
FIG. 32 shows a safety IV catheter assembly that is formed in accordance with an alternate embodiment of the present invention.
FIG. 33 is a side view of the catheter assembly of FIG. 32.
Figure 34:
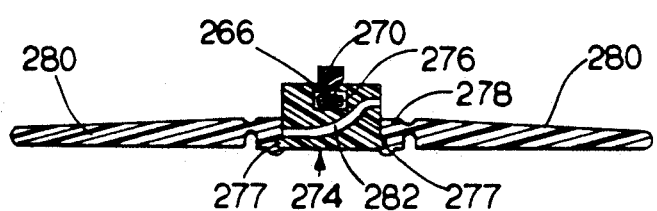
FIG. 34 is a cross-section taken along lines 34—34 of FIG. 32.

FIGS. 32-37 of the drawings illustrate a safety IV catheter assembly 265 that is formed in accordance with an alternate embodiment of the present invention. Referring concurrently to FIGS. 32-34, the catheter assembly 265 is shown in the as-packaged configuration including a sharp trocar 266 of solid cross-section to make a veni puncture through the patient's tissue and a flexible catheter cannula 268 surrounding trocar 266 in coaxial alignment therewith. Trocar 266 is bonded to a manually operable trocar position control button 270. Position control button 270 is received within and slidable through an elongated track 272 that is formed within a disposable, molded plastic safety housing 274. As will soon be described when referring to FIG. 35, position control button 270 is movable rearwardly through track 270 to relocate trocar 266 from an axially extended position (as shown), at which to penetrate the patient's tissue, to a retracted position, at which the trocar is completely surrounded and shielded within a longitudinally extending channel 276 of safety housing 274.

Safety housing 274 includes an integral circular flange 277 that is snap-fit within and movable through a corresponding groove formed in a flat wing base 278 (best shown in FIG. 34), such that housing 274 can be rotated relative to said wing base. Coextensively formed with and extending in opposite directions from wing base 278 is a pair of flexible stabilizing wings 280 that are to be taped to the patient's skin so as to prevent a premature removal of cannula 268 from the patient's vein. Safety housing 274 also includes a laterally extending flow path 282 that is molded therewithin and, in the as packaged configuration of FIGS. 32-34 is arranged in substantially perpendicular alignment with catheter cannula 268 and a flexible fluid tube 284 that is to be fluidically coupled to one or more of the medication bags from the IV system shown in FIG. 2. Thus, in the as-packaged configuration, flow path 282 is positioned to interrupt the flow of fluid between fluid tube 284 and cannula 268. However, and as will be disclosed in greater detail hereinafter, safety housing 274 may be rotated relative to wing base 278 from the as-packaged configuration to an active configuration, at which fluid path 282 will be aligned with cannula 268 and fluid tube 284 so as to complete the fluid path between the medication bags and said cannula.

As will also be disclosed in greater detail hereinafter, the safety housing 274 is adapted to be detached from wing base 278 after the trocar 266 has been retracted into the channel 276 thereof and housing 274 has been rotated to the active configuration. To this end, the safety housing 274 is provided with a pair of narrow, laterally extending slits 286 at which to establish a weakened area of reduced cross-section so as to permit housing 274 to be fractured thereat and removed from catheter assembly 265 for disposal.

Figure 35:
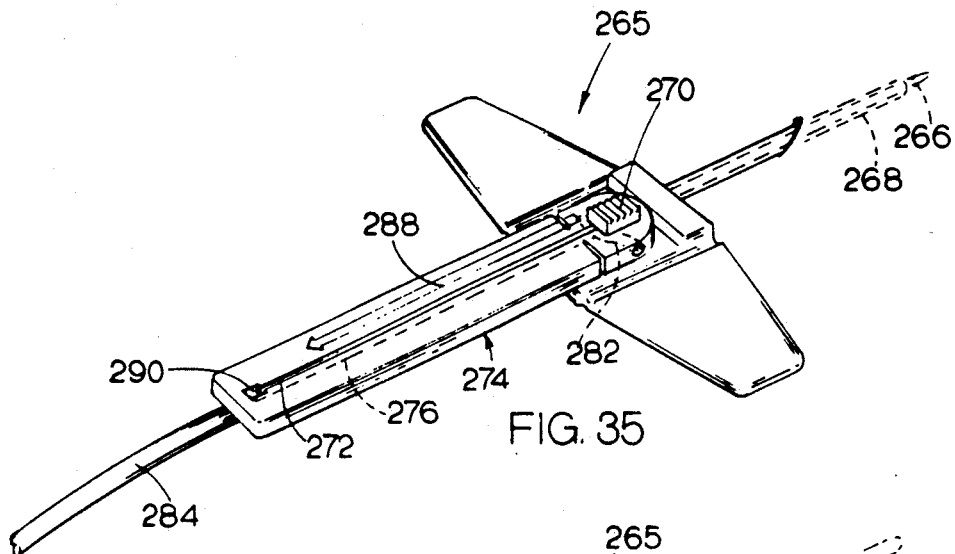
FIGS. 35-37 illustrate the operation of the safety IV catheter assembly of FIGS. 32-34.
Figure 36:
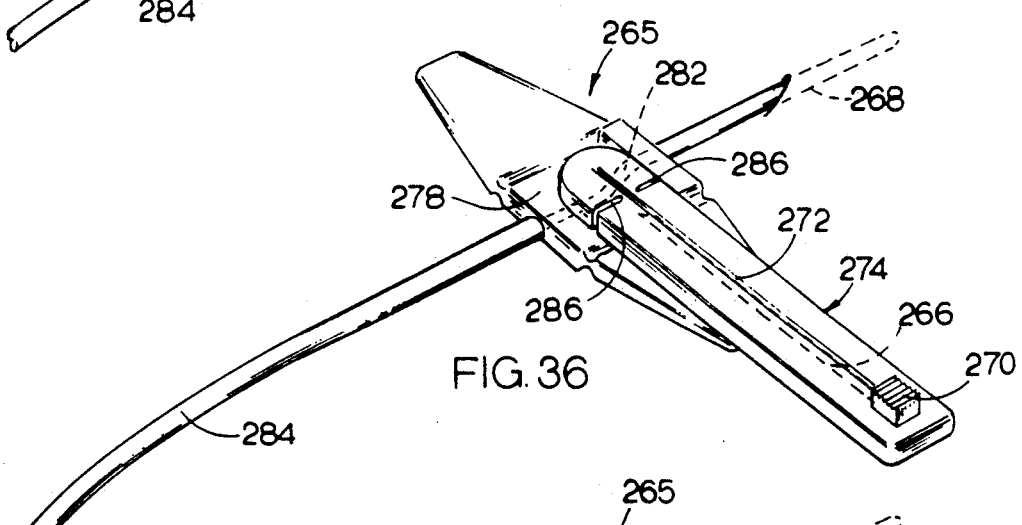
Figure 37:
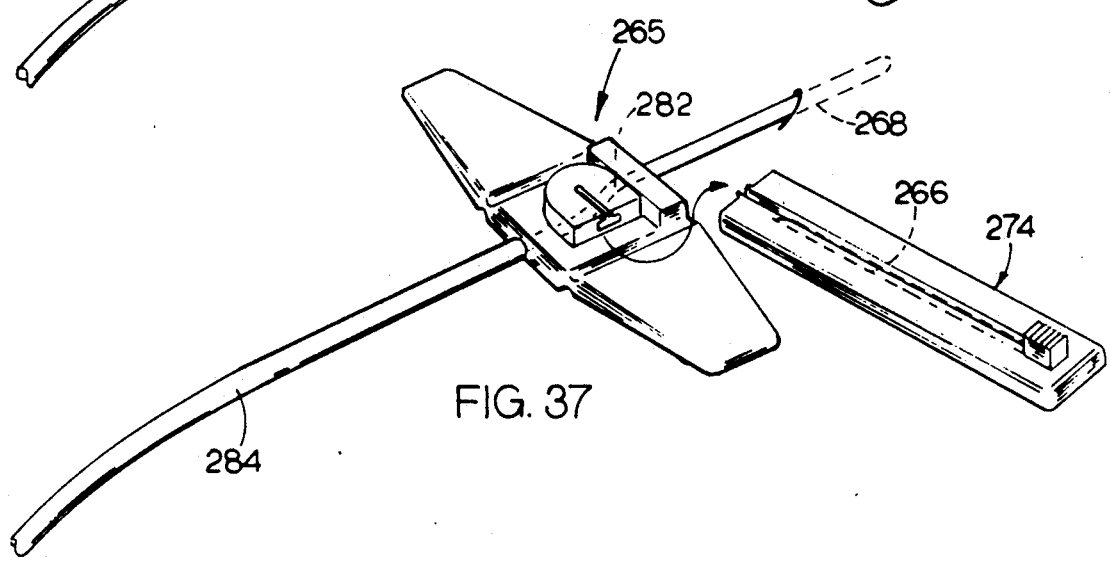

The operation of catheter assembly 265 is now described while referring to FIGS. 35-37. In FIG. 35, the sharp trocar 266 has made a veni puncture through the patient's tissue to locate the catheter cannula 268 within a vein of the patient. The safety housing 274 is initially in the as-packaged configuration with the laterally extending flow path 282 thereof positioned to block the flow of fluid between cannula 268 and fluid tube 284, so as to prevent blood backflash.

In order to retract the trocar 266 into safety housing 274, a pushing force is applied to the trocar position control button 270 in the direction indicated by reference arrow 288. Accordingly, position control button 270 is moved rearwardly through the elongated track 272 in safety housing 274. The rearward movement of control button 270 through track 272 causes a corresponding movement of trocar 266 into the longitudinally extending channel 276 within housing 274. A locking detent 290 is formed at the end of track 272 for receipt of the position control button 270 so as to prevent both a forward movement of said button through track 272 and an inadvertent return of trocar 266 to the as-packaged configuration of FIGS. 35-37. Accordingly, with control button 270 moved to and retained in locking detent 290, the trocar 266 will be completely, shielded and rendered inaccessible within the channel 276 of safety housing 274.

In FIG. 36, after the trocar position control button 270 has been moved rearwardly through track 272 for receipt within the locking detent (290 in FIG. 35) and trocar 266 has been retracted into the channel (276 in FIG. 35) of safety housing 274, said housing is rotated 90 degrees around wing base 278 to the active configuration. Hence, the laterally extending fluid path 282 through safety housing 274 is rotated into alignment with fluid tube 284 and catheter cannula 268 to complete a flow path therebetween.

In FIG. 37, an upward bending force is applied to the safety housing 274, into which trocar 266 has been retracted, so as to break said housing at the weakened area thereof formed between the pair of slits (286 in FIG. 36). Thus, housing 274 may be detached from catheter assembly 265 and safely discarded without handling the trocar 266. Accordingly, an accidental needle stick and the possible spread of infectious disease are advantageously avoided The remainder of the catheter assembly 265 is unaffected by the detachment and disposal of safety housing 274, so that fluid can be delivered from the medication bags of the IV system of FIG. 2 to the patient via fluid tube 284, flow path 282 and catheter cannula 268.

It will be apparent that while a preferred embodiment of the invention has been shown and described, various modifications and changes may be made without departing from the true spirit and scope of the invention.

Having thus set forth the embodiments of the present invention, what is claimed is:

1. For use in an IV system including a medication bag having a fluid compartment in which a supply of fluid to be delivered to a patient is packaged and a platen surrounding and supporting said fluid compartment, fluid delivery means by which to deliver fluid from the fluid compartment of the medication bag to the patient, and flexible fluid tubing means fluidically connected between the fluid compartment of the medication bag and the fluid delivery means, the improvement of flow control means located within said platen and positioned between said fluid compartment and said delivery means by which to regulate the rate at which fluid is supplied therebetween, said flow control means comprising means by which to apply a compressive force to the fluid tubing means to change the cross-sectional flow area thereof, such that the rate at which fluid is supplied to said fluid delivery means is dependent upon the compressive force applied to said tubing means.

2. The flow control means recited in claim 1, including:
   a pressure regulating knob disposed at one side of the fluid tubing means;
   a pressure regulating base located at the opposite side of said tubing means in spaced opposition to said pressure regulating knob; and
   means by which to interconnect said knob and said base so that said tubing means is received in the space therebetween,
   said knob being moved towards said base to reduce the space therebetween and apply a compressive force to said tubing means to change the cross-sectional flow area thereof.

3. The flow control means recited in claim 2, wherein said pressure regulating knob includes a pressure producing stem extending therefrom to be moved into contact with and apply the compressive force to the fluid tubing means when said knob is moved towards said pressure regulating base.

4. The flow control means recited in claim 2, wherein said pressure regulating knob and said pressure regulating base include respective screw threaded connecting members that are mated together to form said means by which to interconnect said knob and said base, such that a rotation of said knob relative to said base causes a corresponding movement of said knob towards said base to increase the compressive force applied to the fluid tubing means and thereby vary the cross-sectional flow area thereof.

5. The flow control device recited in claim 4, wherein the respective connecting members of said pressure regulating knob and said pressure regulating base are located at opposite sides of the platen of the medication bag and mated together by way of an opening through said platen.

6. The flow control means recited in claim 1, including:
   a pressure control plate located at one side of the fluid tubing means;
   a pressure control disc located at the opposite side of said tubing means in spaced opposition to said pressure control plate, such that said tubing means is received in the space between said plate and said disc, and said disc is movable towards said plate to reduce the space therebetween and apply a compressive force to said tubing means to change the cross-sectional flow area thereof; and
   locking means by which to releasably engage said pressure control disc as said disc is moved towards said pressure control plate to prevent a relocation of said disc and maintain the compressive force applied to the tubing means.

7. The flow control means recited in claim 6, further including a pressure release hub extending between said pressure control plate and said pressure control disc, said locking means projecting from said hub for releasably engaging said disc as said disc is moved towards said plate.

8. The flow control means recited in claim 7, wherein said pressure release hub is pivotally connected to said pressure control plate and rotatable relative to said pressure control disc so as to move said locking means out of engagement with said disc to permit a relocation of said disc.

9. The flow control means recited in claim 8, further including spring means located between said pressure control plate and said pressure control disc to bias said disc for movement away from said plate when said pressure release hub is rotated and said locking means is moved out of engagement with said disc.

10. The flow control means recited in claim 7, wherein said pressure control plate and said pressure control disc are located at opposite sides of the platen of the medication bag, and said pressure release hub extends through an opening in said platen between said plate and said disc.

11. The flow control means recited in claim 1, including a flow control regulator having a pair of flow control surfaces arranged in spaced opposition to one another, such that the distance between said flow control surfaces varies along the length of said regulator,
   said fluid tubing means being received between said pair of flow control surfaces, and said flow control regulator being moved relative to said tubing means to apply a compressive force to said tubing means and change the cross-sectional flow area thereof depending upon the location of said regulator and the corresponding distance between said flow control surfaces relative to the position of said tubing means.

12. The flow control means recited in claim 11, wherein said flow control regulator is rotated relative to said fluid tubing means.

13. The flow control means recited in claim 11, wherein first ends of said flow control surfaces are connected together such that said flow control regulator has a V-shaped configuration.

14. The flow control means recited in claim 11, wherein the flow control surfaces of said flow control regulator are located at opposite sides of the platen of the medication bag and connected together at first ends thereof through an opening in said platen.

15. The flow control means recited in claim 1, including a flow control bar comprising:
- a pressure control surface located at one side of the fluid tubing means;
- a support surface located at the opposite side of the fluid tubing means in spaced opposition to said pressure control surface such that said tubing means is received in the space therebetween; and
- at least one pressure control bump positioned at a particular location of said pressure control surface and extending towards said support surface,
- said flow control bar being moved relative to the fluid tubing means to apply a compressive force to said tubing means and change the cross-sectional flow area thereof when the pressure control bump of said pressure control surface is moved into contact with said tubing means.

16. The flow control means recited in claim 15, wherein the pressure control and support surfaces of said flow control bar are located at opposite sides of the platen of the medication bag and connected together through an opening in said platen.

17. The flow control means recited in claim 16, wherein said flow control bar slides through the opening in the platen so that said pressure control surface moves over said platen for selectively moving said pressure control bump thereof into and out of contact with the fluid tubing means.

18. The flow control means recited in claim 1, including at least one flexible pressure control flap to be folded around the fluid tubing means, and
- fastening means by which to retain said pressure control flap folded around the fluid tubing means so as to apply a compressive force to said tubing means and change the cross-sectional flow area thereof.

19. The flow control means recited in claim 18, wherein said pressure control flap is received in and rotatable out of an opening in said platen of the medication bag to be folded around the fluid tubing means.

20. A medication bag to be interconnected with an IV catheter and having a fluid compartment in which fluid is packaged for delivery to a patient by way of a catheter, said medication bag comprising a platen to surround and support said fluid compartment, a fluid tube molded into said platen and communicating fluidically with said fluid compartment and the catheter so that the fluid packaged in said compartment can be supplied to the catheter, and drip chamber means molded into said platen and communicating with said fluid tube so as to regulate the rate at which fluid is supplied from said fluid compartment to said catheter via said fluid tube.

21. The medication bag recited in claim 20, wherein the fluid compartment is manufactured from a relatively rigid, and inflexible material, said bag further comprising vent means communicating with said compartment through which air may pass for forcing the fluid packaged in the compartment outwardly thereof and into said fluid tube.

22. A flow control device for use in an IV system including a medication bag having a fluid compartment in which fluid is stored for delivering to a patient and a platen surrounding and supporting said fluid compartment, fluid delivery means by which to delivery fluid from said compartment to the patient, and flexible tubing means fluidically connected between said fluid compartment and said fluid delivery means to supply fluid therebetween, said flow control device comprising:
- a pressure regulating knob located at one side of said platen in contact with one side of said tubing means;
- a pressure regulating base located at the opposite side of said platen in contact with the opposite side of said tubing means; and
- means to interconnect said knob to said base by way of an opening through said platen, such that said knob is movable towards said base for applying a compressive force to said tubing means to change the cross-sectional flow area thereof, the rate at which fluid is supplied from said fluid compartment to said fluid delivery means being dependent upon the compressive force applied to said tubing means.

* * * * *